(12) United States Patent
Castro et al.

(10) Patent No.: US 7,759,519 B2
(45) Date of Patent: Jul. 20, 2010

(54) AMIDE AND PEPTIDE DERIVATIVES OF DIALKYLENETRIAMINES AND THEIR USE AS TRANSFECTION AGENTS

(75) Inventors: Mariano Javier Castro, Cambridge (GB); Christopher Kitson, Stevenage (GB); Mark Ladlow, Cambridge (GB); Alpesh Patel, Cambridge (GB)

(73) Assignee: Glaxo Group Limited, Brentford, Middlesex (GB)

( * ) Notice: Subject to any disclaimer, the term of this patent is extended or adjusted under 35 U.S.C. 154(b) by 476 days.

(21) Appl. No.: 11/719,449

(22) PCT Filed: Nov. 17, 2005

(86) PCT No.: PCT/EP2005/012460

§ 371 (c)(1),
(2), (4) Date: May 16, 2007

(87) PCT Pub. No.: WO2006/053782

PCT Pub. Date: May 26, 2006

(65) Prior Publication Data

US 2009/0209472 A1   Aug. 20, 2009

(30) Foreign Application Priority Data

Nov. 19, 2004 (GB) ................... 0425555.0

(51) Int. Cl.
```
C07C 233/05    (2006.01)
C07C 233/09    (2006.01)
C07C 235/00    (2006.01)
C07C 237/00    (2006.01)
C12N 15/63     (2006.01)
C12N 15/64     (2006.01)
```

(52) U.S. Cl. .................. 564/153; 564/159; 435/455

(58) Field of Classification Search ................ None
See application file for complete search history.

(56) References Cited

U.S. PATENT DOCUMENTS 6,191,101 B1   2/2001   Jacques et al.

FOREIGN PATENT DOCUMENTS

DE           2102470        8/1972

OTHER PUBLICATIONS

Database CAPLUS on STN, Acc. No. 1972:526025, Nottes, DE 2102470 (Aug. 3, 1972) (abstract).*
Yinkyongnarongkul, Boon, et al. "Solid-phase synthesis of 89 polyamine-based cationic lipids for DNA delivery to mammalian cells." Retrieved from STN Database accession No. 2004:98933 abstract & Chemistry-A European Journal, 10(2), 463-473 Coden: CEUIED; ISSN: 0947-6539 (2004).
How, S.E., et al., "Polyplexes and lipoplexes for mammalian gene delivery: from tradition to microarray screen." Retrieved from STN Database accession No. 2004:713304 abstract & Combinatorial Chemistry and High Throughput screen, 7(5), 423-430 Coden: CCHSFU; ISSN: 1386-2073 (2004).
Kim, Kyoung Taek et al., "Self-organization of dendron-poly(ethylene glycol) conjugates in an aqueous phase." Retrieved from STN Database accession No. 2004:1040568 abstract & Macromolecular Research, 12(5), 528-533 Coden: MRAECT; ISSN: 1598-5032 (2004).
Ko, Hae Seung et al., <<Supramolecular Self-assembly of Dimeric Dendrons with Aromatic Bridge Units. Retrieved from STN Database accession No. 2004-729308 abstract & Chemistry of Materials, 16(20), 3872-3876 Coden: CMATEX; ISSN: 0897-4756, (2004).
Kato, Tadahiko et al., "Fabric softeners containing linear, cyclized, and condensed amides." Retrived from STN Database accession No. 2003:17438 abstract & JP 2003 003369 A2 (Nikka Chemical Industry Co., Ltd., Japan (Jan. 8, 2003).
Komatsu, Yukio et al., "Treatment agents for synthetic fibers as precursors for manufacture of carbon fibers." Retrived from STN Database accession No. 2001:563821 abstract & JP 2001 207380A2 (Takemoto Oil and Fat Co., Ltd., Japan) (Aug. 3, 2001).
Kim, Chulhee et al., "Supramolecular Assembly of Amide Dendrons." Retrieved from STN Database accession No. 2001: 345107 abstract & Journal of the American Chemical Society, 123(23), 5586-5587 Coden: JACSAT; ISSN: 0002-7863, (2001).
Takagi, Makoto et al. "Compositions for oiling and softening synthetic fibers and method for using." Retrieved from STN Database accession No. 2001:218034 abstract & JP 2001 081673A2 (Takemoto Oil and Fat Co., Ltd., Japan) (Mar. 27, 2001).
Popaj, Kasim et al. "Synthetic analogues to the spermidine-spermine alkaloid tenuilobine." Retrieved from STN Dtabase accession No. 2000:882203 abstract & Helvetica Chimica Acta, 83(11), 3021-3034 Coden: HEACAV; ISSN: 0018-109X, (2000).
Doll, Martin K-H et al. "Tenuilobine-a new polyamine alkaloid from Oncinotis Tenuiloba." Retrieved from STN Database accession No. 1996:94635 abstract & Heterocycles, 42(1), 319-24 Coden: HYCYAM; ISSN: 0385-5414 (1996).
Janoat, Vaclav et al. "Molecular umbrellas." Retrieved from STN Database accession No. 1996:62571 absract & Journal of the Ermican Chemical Society, 118(6), 1573-4 Coden: JACSAT; ISSN: 0002-7863, (1996).
Chulhee, Kim et al. Supramolecular Assembly of Amide Dendeons. J. Am. Chem. Soc., vol. 123, pp. 5586-5587, (2001).

* cited by examiner

*Primary Examiner*—Brian J Davis
(74) *Attorney, Agent, or Firm*—Reid S. Willis; John Lemanowicz

(57) ABSTRACT

This invention relates to newly identified spermidine based surfactant compounds, to the use of such compounds and to their production. The invention also relates to the use of the spermidine based compounds to facilitate the transfer of polynucleotides into cells.

16 Claims, 12 Drawing Sheets

*Reagents & conditions:* a) $CF_3CO_2Et$, $H_2O$, MeCN, reflux; b) $Boc_2O$, $^iPr_2NEt$, THF, rt; c) $NaOH-H_2O$, MeOH, 10 °C - rt; d) $RCO_2NSuc$, $K_2CO_3$, THF, $H_2O$, rt; e) $CF_3CO_2H$, $CH_2Cl_2$, rt.

*Reagents & conditions:* a) CF$_3$CO$_2$Et, H$_2$O, MeCN, reflux; b) Br(CH$_2$)$_p$CO$_2$R, $^i$Pr$_2$NEt, MeCN, rt; c) NaOH-H$_2$O, MeOH, rt; d) Boc$_2$O, H$_2$O, MeOH, rt.

*Reagents & conditions:* a) MeOCOCl, NaOH-H$_2$O, THF, rt; b) 10% Pd/C, $^c$HCl, MeOH, H$_2$, 5 bar; c) Boc$_2$O, $^i$Pr$_2$NEt, DMF; d) 2N KOH-H$_2$O, THF, rt.

*Reagents & conditions:* a) (PG)$_y$(Aa)$_x$, HCTU, $^i$PrNEt$_2$, DMF, rt; b) 5N HCl-EtOAC, CH$_2$Cl$_2$, rt.

18 a

19 b

20

*Reagents & conditions:* a) $(PG)_y(Aa)_x$, HCTU or HBTU, $^iPr_2NEt$, DMF, rt.; b) 5N HCl-EtOAc, $CH_2Cl_2$, rt.

AMIDE AND PEPTIDE DERIVATIVES OF DIALKYLENETRIAMINES AND THEIR USE AS TRANSFECTION AGENTS

This application claims the benefit of PCT/EP2005/012460, filed 17 Nov. 2005.

This invention relates to newly identified spermidine based surfactant compounds, to the use of such compounds and to their production. The invention also relates to the use of the spermidine based compounds to facilitate the transfer of polynucleotides into cells or to facilitate the transfer of therapeutically active compounds into cells for drug delivery. Compounds with properties related to properties of compounds of the invention are often referred to as Gemini surfactants.

Surfactants are substances that markedly affect the surface properties of a liquid, even at low concentrations. For example surfactants will significantly reduce surface tension when dissolved in water or aqueous solutions and will reduce interfacial tension between two liquids or between a liquid and a solid. This property of surfactant molecules has been widely exploited in industry, particularly in the detergent and oil industries. In the 1970s a new class of surfactant molecule was reported, characterised by two hydrophobic chains with polar heads which are linked by a hydrophobic bridge (Deinega, Y et al., *Kolloidn. Zh.* 36, 649, 1974). These molecules, which have been termed "gemini" (Menger, F M and Littau, C A, *J. Am. Chem. Soc.* 113, 1451, 1991), have very desirable properties over their monomeric equivalents. For example they are highly effective in reducing interfacial tension between oil and water based liquids and have a very low critical micelle concentration (Menger, F M and Keiper, J S, *Angewandte. Chem. Int. Ed. Engl.*, 2000, 39, 1906).

Cationic surfactants have been used inter alia for the transfection of polynucleotides into cells in culture, and there are examples of such agents available commercially to scientists involved in genetic technologies (for example the reagent Tfx™-50 for the transfection of eukaryotic cells available from Promega Corp. WI, USA).

The efficient delivery of DNA to cells in vivo, either for gene therapy or for antisense therapy, has been a major goal for some years. Much attention has concentrated on the use of viruses as delivery vehicles, for example adenoviruses for epithelial cells in the respiratory tract with a view to corrective gene therapy for cystic fibrosis (CF). However, despite some evidence of successful gene transfer in CF patients, the adenovirus route remains problematic due to inflammatory side-effects and limited transient expression of the transferred gene. Several alternative methods for in vivo gene delivery have been investigated, including studies using cationic surfactants. Gao, X et al. *Gene Ther.* 2, 710-722, 1995 demonstrated the feasibility of this approach with a normal human gene for CF transmembrane conductance regulator (CFTR) into the respiratory epithelium of CF mice using amine carrying cationic lipids. This group followed up with a liposomal CF gene therapy trial which, although only partially successful, demonstrated the potential for this approach in humans (Caplen, N J. et al., *Nature Medicine*, 1, 3946, 1995). More recently other groups have investigated the potential of other cationic lipids for gene delivery (Miller, A, *Angew. Int. Ed. Engl.*, 37, 1768-1785, 1998), for example cholesterol derivatives (Oudrhiri, N et al. *Proc. Natl. Acad. Sci.* 94, 1651-1656, 1997). This limited study demonstrated the ability of these cholesterol based compounds to facilitate the transfer of genes into epithelial cells both in vitro and in vivo, thereby lending support to the validity of this general approach.

The use of non-viral (cationic lipid) vectors for gene transfection has recently been reviewed, see D. Niculescu-Duvaz, J. Heyes and C. J. Springer, *Curr. Med. Chem.*, 2003, 10, 1233.

These studies, and others, show that in this new field of research there is a continuing need to develop novel low-toxicity surfactant molecules to facilitate the effective transfer of polynucleotides into cells both in vitro for transfection in cell-based experimentation and in vivo for gene therapy and antisense treatments. Gemini surfactants based on cysteine (WO99/29712) or on spermine (WO00/77032) or diamine (WO00/76954) have previously been made. Other examples of gemini surfactants are found in WO00/27795, WO02/30957, WO02/50100 and WO03/82809. The use of Gemini surfactants as polynucleotide vectors has recently been reviewed (A. J. Kirby, P. Camilleri, J. B. F. N. Engberts, M. C. Feiters, R. J. M. Nolte, O, Söderman, M. Bergsma, P. C. Bell, M. L. Fielden, C. L. García Rodríguez, Philippe Guédat, A. Kremer, C. McGregor, C. Perrin, G. Ronsin and M. C. P. van Eijk, *Angew. Chem. Int. Ed.*, 2003, 42, 1448, see also R. Zana and J. Xia, *Gemini Surfactants*, Marcel Dekker, NY, 2004)

A recently developed technique involves the use of synthetic short interfering (si) double stranded RNA molecules to transiently suppress gene function. This technique of RNA interference (RNAi), originally coined from work in *C. elegans* (A. Fire, Trends Genet., 1999, 15(9), 358) was later developed such that its use could be applied to mammalian cells (S. M. Elbashir, J. Harborth, W. Lendeckel, A. Yalcin, K. Weber, T. Tuschl, Nature, 2001, 411, 494). The ability to deliver these siRNA effector molecules to the correct location of the majority of a cell population is a key step in the effective utilisation of this technology. Once correctly localised the antisense strand of the RNA duplex binds to the complementary region of the targeted messenger (m)RNA (coding for the target of interest), leading to hydrolysis of the mRNA and its subsequent degradation. This transient reduction in mRNA leads to a transient reduction in target gene expression. Highly efficient delivery and correct localisation are required to reduce target gene expression to levels such that the function of the target can be elucidated.

The present invention seeks to overcome the difficulties exhibited by existing compounds.

The invention relates to compounds having the general structure of formula (I):

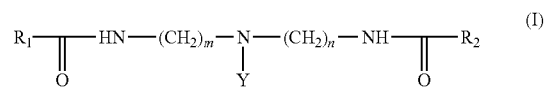

where Y is either:

$(Aa)_x$ or a group of formula (II)

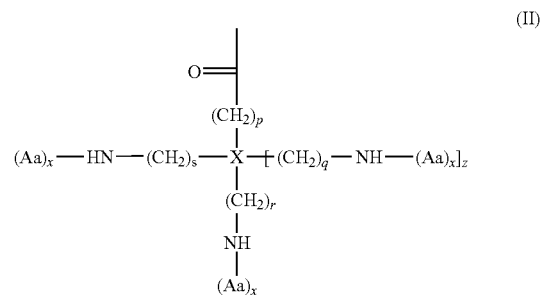

wherein $R_1$ and $R_2$, which may be the same or different, is a saturated or unsaturated, linear or branched hydrocarbon chain of up to 24 carbon atoms;

m is 1 to 10;

n is 1 to 10;

$(Aa)_x$, which may be the same or different at each occurrence, is x natural or unnatural amino acids linked in a linear or branched manner;

x, which may be the same or different at each occurrence, is 1 to 6;

p is 0 to 6;
q is 1 to 6;
r is 1 to 6;
s is 1 to 6;
z is 0 or 1;

X is N, CH or C with the proviso that when X is N, z is 0 or 1; when X is CH, z is 0; and when X is C, z is 1;

or a salt, preferably a pharmaceutically acceptable salt thereof.

Preferably m is 3 to 6, most preferably 4.
Preferably n is 3 to 6, most preferably 3.

In one embodiment a) Y is $(Aa)_x$. In such an embodiment, $R_1$ and $R_2$ may, for example, be the same. (Aa) is preferably a basic amino acid. Examples of basic amino acids include $[H_2N(CH_2)_3]_2N(CH_2)CO_2H$, $(H_2NCH_2)_2CHCO_2H$, or L or D enantiomers of Ser (serine), Lys (lysine), Orn (ornithine), Dab (diamino butyric acid) or Dap (diamino propionic acid). Examples of basic amino acids include amino acids comprising at least one $NH_2$ group (or optionally an OH group) in the side chain and comprising from 1 to 12, for example from 1 to 10 carbon atoms.

Preferably x is 1 to 4, more preferably 1 or 2, most preferably 1.

In another embodiment b) Y is a group of formula (II)

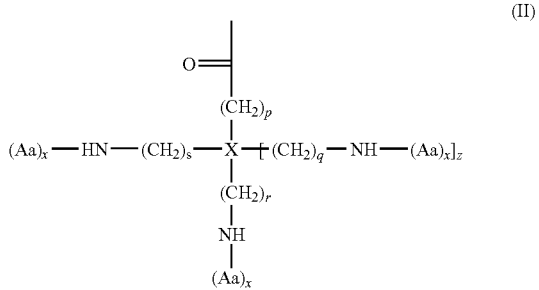

where x, which may be the same or different at each occurrence, is 1 to 6;

p is 0 to 6;
q is 1 to 6;
r is 1 to 6;
s is 1 to 6;
z is 0 or 1;

X is N, CH or C with the proviso that when X is N, z is 0 or 1; when X is CH, z is 0; and when X is C, z is 1.

In an example of embodiment (b) X may for example be N. In one such embodiment z is 0 and r and s may, for example, be the same and $R_1$ and $R_2$ may, for example, be the same.

In one embodiment, X is N or C.

(Aa) is preferably a basic amino acid. Examples of basic amino acids include $[H_2N(CH_2)_3]_2N(CH_2)CO_2H$, $(H_2NCH_2)_2CHCO_2H$, or L or D enantiomers of Ser (serine), Lys (lysine), Orn (ornithine), Dab (diamino butyric acid) or Dap (diamino propionic acid). Examples of basic amino acids include amino acids comprising at least one $NH_2$ group (or optionally an OH group) in the side chain and comprising from 1 to 12, for example from 1 to 10 carbon atoms.

Preferably x is 1 to 4, more preferably 1 or 2, most preferably 1. In one embodiment of (b) x is the same at each occurrence. In another embodiment x is different at each occurrence.

Preferably p is 1.
Preferably q is 1 or 3.
Preferably r is 1 or 3.
Preferably s is 1 or 3.

In a further preferred embodiment the $R_1$ or $R_2$ saturated or unsaturated, linear or branched hydrocarbon chain of up to 24 carbon atoms has 10 or more carbon atoms, for example 12 or more, for example 14 or more, for example 16 or more carbon atoms. In a further preferred embodiment the $R_1$ or $R_2$ saturated or unsaturated, linear or branched hydrocarbon chain of up to 24 carbon atoms is selected from:

—$(CH_2)_{10}CH_3$

—$(CH_2)_{12}CH_3$

—$(CH_2)_{14}CH_3$

—$(CH_2)_{16}CH_3$

—$(CH_2)_{18}CH_3$

—$(CH_2)_{20}CH_3$

—$(CH_2)_7CH=CH(CH_2)_7CH_3$ natural mixture

—$(CH_2)_7CH=CH(CH_2)_5CH_3$ natural mixture

—$(CH_2)_7CH=CH(CH_2)_5CH_3$ Cis

—$(CH_2)_7CH=CH(CH_2)_7CH_3$ Cis

—$(CH_2)_7CH=CH(CH_2)_5CH_3$ Trans

—$(CH_2)_7CH=CH(CH_2)_7CH_3$ Trans

—$(CH_2)_7CH=CHCH_2CH=CH(CH_2)_4CH_3$

—$(CH_2)_7(CH=CHCH_2)_3CH_3$

—$(CH_2)_3CH=CH(CH_2CH=CH)_3(CH_2)_4CH_3$

—$(CH_2)_7CHCH(CH_2)_7CH_3$

—$CH_2CH(CH_3)[CH_2CH_2CH_2CH(CH_3)]_3CH_3$ or —$(CH_2)_{22}CH_3$.

Most preferably the hydrocarbon chain is selected from $(CH_2)_7CH=CH(CH_2)_7CH_3$ natural mixture, $(CH_2)_7CH=CH(CH_2)_7CH_3$ Cis and $(CH_2)_7CH=CH(CH_2)_7CH_3$ Trans.

In one embodiment, a compound of the invention is a so-called 'Gemini' surfactant compound. That is to say that the compound is symmetrical with at least two aliphatic chains.

Compounds of the present invention may be prepared from readily available starting materials using synthetic chemistry well known to the skilled person. FIG. 1 shows a general scheme for the synthesis of an intermediate 6 for the synthesis of compounds of the invention. FIG. 2 shows a general scheme for the synthesis of a protected preferred (Aa) group 9 for the synthesis of compounds of the invention. FIG. 3 shows a general scheme for the synthesis of a protected preferred (Aa) group 14 for the synthesis of compounds of the invention.

As shown in the general scheme of FIG. 4, reaction of the intermediate 6 by addition of $(Aa)_x$ groups under appropriate conditions followed by deprotection produces molecules with the substitution pattern according to embodiment a) of the invention.

FIG. 5 shows a general scheme for the conversion of intermediate 6 to advanced intermediate 18 for the synthesis of compounds of the invention. As shown in the general scheme of FIG. 6, intermediate 18 may be used to produce molecules with the substitution pattern according to embodiment b) of the invention, by addition of $(Aa)_x$ groups under appropriate conditions followed by deprotection.

Various alternative strategies are well known to the skilled person and suitable strategies may be devised for any particular desired final substitution pattern. For asymmetric substitution patterns, physical separation of products or intermediates may be necessary. Suitable separation methods, for example chromatographic methods, are well known to the person skilled in the art.

Salts of molecules in accordance with the invention may be prepared by standard techniques, as shown for example in the schemes in FIGS. 4 and 6. In the scheme shown in FIGS. 4 and 6, the salt formation step is also a deprotection step.

Another aspect of the invention relates to methods for using the spermidine based surfactant compounds. Such uses include facilitating the transfer of oligonucleotides and polynucleotides into cells for antisense, gene therapy and genetic immunisation (for the generation of antibodies) in whole organisms. Other uses include employing the compounds of the invention to facilitate the transfection of polynucleotides into cells in culture when such transfer is required, in, for example, gene expression studies and antisense control experiments among others. Protocols for the preparation of such polynucleotides and antisense molecules are well known in the art (for example Sambrook et al., Molecular Cloning: A Laboratory Manual, 2nd Ed., Cold Spring Harbor Laboratory Press, Cold Spring Harbor, N.Y. (1989), Cohen, JS ed. Oligodeoxynucleotides as Antisense Inhibitors of Gene Expression, CRC Press, Boca Raton, Fla. (1989)). The polynucleotides can be mixed with the compounds, added to the cells and incubated to allow polynucleotide uptake. After further incubation the cells can be assayed for the phenotypic trait afforded by the transfected DNA, or the levels of mRNA expressed from said DNA can be determined by Northern blotting or by using PCR-based quantitation methods for example the Taqman® method (Perkin Elmer, Conn., USA).

Compounds of the invention offer a significant improvement, typically between 3 and 6 fold, in the efficiency of cellular uptake of DNA in cells in culture, compared with compounds in the previous art. In the transfection protocol, the spermidine surfactant compound may be used in combination with one or more supplements to increase the efficiency of transfection. Such supplements may be selected from, for example:

(i) a neutral carrier, for example dioleyl phosphatidylethanolamine (DOPE) (Farhood, H., et al (1985) *Biochim. Biophys. Acta*, 1235-1289);

(ii) a complexing reagent, for example the commercially available PLUS reagent (Life Technologies Inc. Maryland, USA) or peptides, such as polylysine or polyornithine peptides or peptides comprising primarily, but not exclusively, basic amino acids such as lysine, ornithine and/or arginine (see for example Henner, W D et al (1973) J. Virol. 12(4) pp 741-747). The list above is not intended to be exhaustive and other supplements that increase the efficiency of transfection are taken to fall within the scope of the invention.

In still another aspect, the invention relates to the transfer of genetic material in gene therapy using the compounds of the invention. For example the skilled person can develop gene delivery methodologies for use in gene therapy, involving the use of spermidine surfactant compounds of the present invention, using protocols that are well known in the art. For example the use of surfactants for delivery of gene transfer vectors to the lung is reviewed in Weiss, D J (2002) Molecular Therapy 6(2) pp 148 to 152.

Yet another aspect of the invention relates to methods to effect the delivery of non-nucleotide based drug compounds into cells in vitro and in vivo using the compounds of the invention.

The following definitions are provided to facilitate understanding of certain terms used frequently herein.

"Amino acid" refers to dipolar ions (zwitterions) of the form $^+H_3NCH(R)CO_2^-$. They are differentiated by the nature of the group R, and when R is different from hydrogen can also be asymmetric, forming D and L families. There are 20 naturally occurring amino acids where the R group can be, for example, non-polar (e.g. alanine, leucine, phenylalanine) or polar (e.g. glutamic acid, histidine, arginine and lysine). In the case of unnatural amino acids R can be any other group which is not found in the amino acids found in nature.

"Polynucleotide" generally refers to any polyribonucleotide or polydeoxyribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNA's or RNA's containing one or more modified bases and DNA's or RNA's with backbones modified for stability or for other reasons. "Modified" bases include, for example, tritylated bases and unusual bases such as inosine. A variety of modifications have been made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Transfection" refers to the introduction of polynucleotides into cells in culture using methods involving the modification of the cell membrane either by chemical or physical means. Such methods are described in, for example, Sambrook et al., *MOLECULAR CLONING: A LABORATORY MANUAL*, 2nd Ed., Cold Spring Harbor Laboratory Press, Cold Spring Harbor, N.Y. (1989). The polynucleotides may be linear or circular, single-stranded or double-stranded and may include elements controlling replication of the polynucleotide or expression of homologous or heterologous genes which may comprise part of the polynucleotide.

A pharmaceutically acceptable acid addition salt can be formed by reaction of a compound of formula (I) with a suitable inorganic or organic acid (such as hydrobromic, hydrochloric, sulfuric, nitric, phosphoric, succinic, maleic, formic, acetic, propionic, fumaric, citric, tartaric, lactic, benzoic, salicylic, glutamic, aspartic, p-toluenesulfonic, trifluoroacetic, benzenesulfonic, methanesulfonic, ethanesulfonic, naphthalenesulfonic such as 2-naphthalenesulfonic, or hexanoic acid), optionally in a suitable solvent such as an organic solvent, to give the salt which is usually isolated for example by crystallisation and filtration. A pharmaceutically acceptable acid addition salt of a compound of formula (I) can comprise or be for example a hydrobromide, hydrochloride, sulfate, nitrate, phosphate, succinate, maleate, formate, acetate, propionate, fumarate, citrate, tartrate, lactate, benzoate, salicylate, glutamate, aspartate, p-toluenesulfonate, trifluoroacetate, benzenesulfonate, methanesulfonate, ethanesulfonate, naphthalenesulfonate (e.g. 2-naphthalenesulfonate) or hexanoate salt.

The invention includes within its scope all possible stoichiometric and non-stoichiometric forms of the salts of the compounds of formula (I) including hydrates and solvates.

Certain compounds of formula (I) are capable of existing in stereoisomeric forms. It will be understood that the invention encompasses all geometric and optical isomers of these compounds and the mixtures thereof including racemates. Tautomers also form an aspect of the invention.

The invention will now be described by way of the following examples. The examples are not to be taken in any way to limit the scope of the invention.

EXAMPLES

Description 1: $N^1,N^8$-Bis(trifluoroacetyl)-spermidine trifluoroacetate (2)

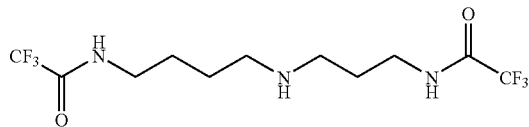

To a solution of spermidine 1 (m=4, n=3; 9.70 g, 66.8 mmol) in CH$_3$CN (150 mL) was added ethyl trifluoroacetate (39.8 mL, 330 mmol) and water (2.8 mL, 18 mmol). The reaction mixture was heated at reflux for 18 h, then allowed to cool to room temperature and the solvent evaporated in vacuo. The residual solid was triturated with CH$_2$Cl$_2$ (2×150 mL) to give the bis(trifluoroacetamide) 2 as a white solid (28.9 g).
LC-MS (ESI): $t_R$=1.10 min (m/z=338.1 [M+H]$^+$).

Description 2: $N^4$-(tert-Butoxycarbonyl)-$N^1,N^8$-bis(trifluoroacetyl)-spermidine (3)

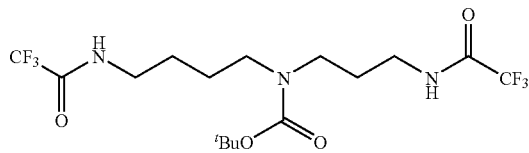

Diisopropylethylamine (16.7 mL, 95.7 mmol) and a solution of di-tert-butyl dicarbonate (14.63 g, 67.0 mmol) in THF (100 mL) were added to a solution of $N^1,N^8$-bis(trifluoroacetyl)spermidine trifluoroacetate 2 (28.8 g, 63.8 mmol) in THF (280 mL) under a nitrogen atmosphere. After 18 h at rt., the solvent was evaporated in vacuo and EtOAc (700 mL) was added. The solution was washed successively with 5% NaHCO$_3$ (2×150 mL), brine (150 mL), 5% KHSO$_4$ (2×150 mL) and brine (2×150 mL), dried over Na$_2$SO$_4$, and evaporated to give the Boc carbamate 3 as white solid (28.0 g). LC-MS (ESI): $t_R$=4.09 min (m/z=438.3 [M+H]$^+$).

Description 3: $N^4$-(tert-Butoxycarbonyl)-spermidine (4)

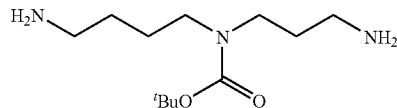

Aqueous sodium hydroxide solution (280 mL×0.5N) was added at 10° C. with stirring to a solution of $N^4$-(tert-butoxycarbonyl)-$N^1,N^8$-bis(trifluoroacetyl)-spermidine (28.0 g, 64.0 mmol) in methanol (400 mL). The cooling bath was removed and the mixture was stirred for 18 h when the methanol was evaporated in vacuo. The resulting aqueous suspension was extracted with [9:1] CHCl$_3$-MeOH (5×300 mL) and the combined organic extracts were dried (Na$_2$SO$_4$) and evaporated in vacuo to leave the amine 4 as a colourless oil (15.5 g).
LC-MS (ESI): $t_R$=0.56 min (m/z=246.2 [M+H]$^+$).

Description 4: $N^1,N^8$-Dioleyl-spermidine trifluoroacetate (6; R=oleyl)

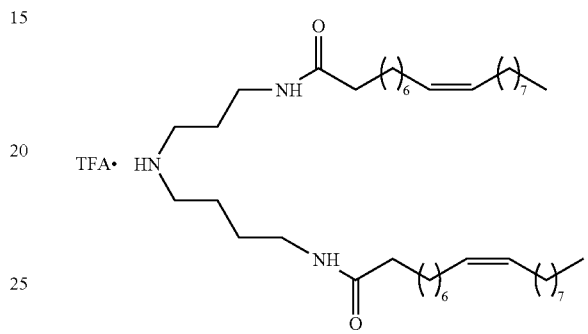

A solution of oleic acid N-hydroxysuccinimide ester (2.10 g, 5.40 mmol) dissolved in THF (90 mL) and a solution of potassium carbonate (890 mg, 6.40 mmol) in water (14 mL) were added to a solution of $N^4$-(tert-butyloxycarbonyl)-spermidine 4 (632 mg, 2.58 mmol) in THF (90 mL). The resulting mixture was stirred at rt. for 16 h and then concentrated in vacuo. The residue was dissolved in CHCl$_3$ (300 mL), washed with 5% aqueous citric acid (50 mL) and brine (2×50 mL), then dried (Na$_2$SO$_4$) and concentrated in vacuo. The resulting oil was purified by flash chromatography eluting with hexane-EtOAc [75:25] followed by hexane-EtOAc [75:25] to afford the intermediate Boc carbamate 5 as a brown oil. The oil was dissolved in CH$_2$Cl$_2$ (6.0 mL), cooled to 0° C. and treated with trifluoroacetic acid (6.0 mL). The resulting mixture was allowed to warm slowly to rt. and stirred for a further 1.5 h. The solvent was removed under reduced pressure, and the residue was co-evaporated with diethyl ether to afford the trifluoroacetate salt 6 as a white solid (1.94 g).

LC-MS (ESI): $t_R$=19.03 min (m/z=674.6564 [M+H]$^+$, 100%); HRMS (ESI) m/z calcd (C$_{54}$H$_{107}$N$_8$O$_4$) 674.6564, found 674.6564 [M+H]$^+$).

Description 5: 2,2,2-Trifluoro-N-{3-[3-(2,2,2-trifluoroacetylamino)-propylamino]propyl}-acetamide trifluoroacetate (7)

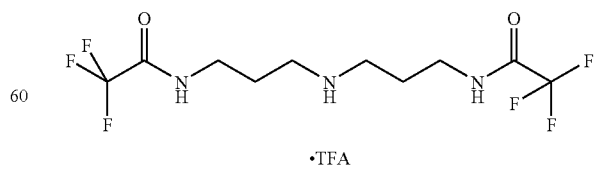

Ethyl trifluoroacetate (27.0 g, 190 mmol) was added to a solution of N'-(3-aminopropyl)propane-1,3-diamine 1 (m=n=3; 5.00 g, 38.2 mmol) in [99:1] acetonitrile:water (150 mL) and the mixture was heated at reflux with stirring for 3 h. After cooling to rt. CH$_2$Cl$_2$ (50 mL) was added and the resulting precipitate was collected and washed with CH$_2$Cl$_2$ (50 mL) to afford the trifluoroacetate salt 7 as a white powder (16.6 g).

LC-MS (ESI): $t_R$=2.05 min (m/z=323.0 [M+H$^+$]).

Description 6: {Bis-[3-(2,2,2-trifluoroacetylamino)propyl]-amino}-acetic acid ethyl ester (8)

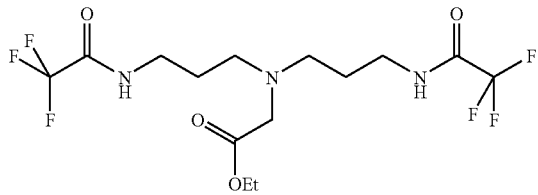

Ethyl bromoacetate (7.30 g, 43.7 mmol) was added to a solution of diisopropylethylamine (15.0 g, 86.3 mmol) and the trifluoroacetate salt 8 (15.0 g, 34.5 mmol) in anhydrous acetonitrile (150 mL). The resulting mixture was stirred at rt. for 18 h and then concentrated in vacuo. The residue obtained was diluted with water (100 mL) and extracted with CH$_2$Cl$_2$ (2×60 mL). The combined organic extracts were dried (Na$_2$SO$_4$) and evaporated in vacuo to give the ethyl ester 8 as a pale yellow oil (14.1 g).

LC-MS (ESI): $t_R$=3.0 min (m/z=410 [M+H$^+$]).

Description 7: Bis-(3-tert-butoxycarbonylamino-propyl)-amino]-acetic acid (9)

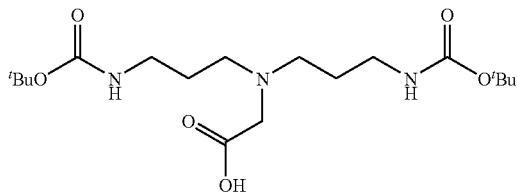

A mixture of the ethyl ester 8 (14.1 g, 34.5 mmol), sodium hydroxide (6.0 g, 40.0 mmol), water (35 mL) and ethanol (175 mL) was stirred at rt. for 20 h. Boc anhydride (15.1 g, 68.8 mmol) was added and stirring was continued for a further 3 h before the mixture was adjusted to neutral pH by adding 10% hydrochloric acid. Water (100 mL) was added and the solution was extracted with CH$_2$Cl$_2$ (4×50 mL). The combined organic extracts were dried (Na$_2$SO$_4$) and concentrated in vacuo to leave the carboxylic acid 9 as a white powder (3.5 g).

LC-MS (ESI): $t_R$=3.05 min (m/z=390.3 [M+H$^+$]).

Description 8: Methyl Dicyanoacetate Potassium Salt (11)

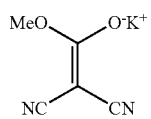

A solution of malononitrile (4.00 g, 60.6 mmol) and methyl chloroformate (4.95 mL, 64.2 mmol) in THF (9.0 mL) was added over 0.5 h to a stirring solution of potassium hydroxide (6.80 g, 121 mmol) in water (6.0 mL) maintaining the temperature below 40° C. The mixture was stirred at rt. for a further 2 h and the resulting precipitate was collected by filtration and washed first with cold water (10 mL) and then ethanol (10 mL) to afford the potassium salt 11 as a white solid (3.31 g).

$^1$H-NMR (D$_2$O): $\delta_H$ 3.58 (s, 3H).

Description 9: Methyl 3-amino-2-(aminomethyl)propionate bis-hydrochloride (12)

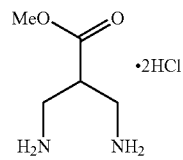

A stirring suspension of 10% palladium on carbon (2.0 g) in a solution of the sodium salt of methyl dicyanoacetate (1.00 g, 6.20 mmol) in methanol (100 mL) containing conc$^d$ hydrochloric acid (32%, 2.0 mL) was hydrogenated at 5 bar and rt. for 24 h. The catalyst was removed by filtration and the solvent was evaporated in vacuo. The residue was treated with methanol (50 mL) and the precipitated sodium chloride was removed by filtration. The solution was concentrated to a low volume in vacuo and then EtOAc was added to precipitate the bis-hydrochloride 12 as an off-white solid (1.20 g).

$^1$H-NMR (d$^6$ DMSO): $\delta_H$ 8.40 (brs, 6H), 3.65 (s, 3H), 3.25 (m, 1H), 3.15 (m, 4H).

Description 10: 3-(tert-Butoxycarbonylamino)-2-(tert-butoxycarbonylamino-methyl)propionic acid methyl ester (13)

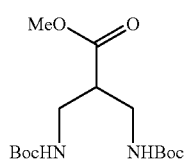

Boc anhydride (0.62 g, 2.83 mmol) was added to a stirring solution of diisopropylethylamine (0.95 mL, 5.40 mmol) and the bis-hydrochloride 12 (255 mg, 1.35 mmol) in DMF (8.0 mL). After stirring for 18 h at rt. the precipitated solids were removed by filtration and the filtrate was evaporated in vacuo. The residual oil was dissolved in EtOAc (30 mL) then washed with water (2×5 mL), dried (Na$_2$SO$_4$) and evaporated in vacuo to afford the bis-Boc carbamate 13 as a viscous colourless oil (430 mg).

$^1$H-NMR (CDCl$_3$): $\delta_H$ 5.20 (brs, 2H), 3.68 (s, 3H), 3.55 (m, 2H), 3.20 (m, 2H), 2.73 (m, 1H), 1.42 (s, 18H).

Description 11: 3-(tert-Butoxycarbonylamino)-2-(tert-butoxycarbonylamino-methyl)propionic acid (14)

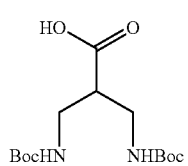

Aqueous 2N sodium hydroxide (2.48 mL, 4.96 mmol) was added to a stirring solution of the methyl ester 13 (0.41 g, 1.24 mmol) in THF (7.5 mL) and the mixture was stirred at rt. for 24 h. Water (15 mL) was added and the solution was acidified with 5% aqueous citric acid. The mixture was extracted with CHCl$_3$ (3×25 mL) and the combined organic extracts were washed with brine (30 mL), dried (Na$_2$SO$_4$), and evaporated in vacuo to leave the acid 14 as a viscous, colourless oil (280 mg).

$^1$H-NMR (d$_6$ DMSO): δ$_H$ 12.2 (brs, 1H), 6.70 (brs, 2H), 3.05 (m, 4H), 2.50 (m, 1H), 1.35 (s, 18H).

Description 12: (Boc)$_2$Lys.($^t$BuO)SerOH

A solution of bis-Boc L-lysine N-hydroxysuccinimide (2.54 g, 5.72 mmol) in THF (60.0 mL) was added to a stirring mixture of L-serine tert-butyl ether (1.02 g, 6.30 mmol) and potassium carbonate (1.03 g, 7.44 mmol) in water (12.0 mL). The mixture was stirred at room temperature for 18 h and then concentrated in vacuo. The residue was diluted with CHCl$_3$ (140 mL) and water (140 mL) and adjusted to pH2 with 1N hydrochloric acid. The organic layer was separated and the aqueous phase was extracted with CHCl$_3$ (2×140 mL). The combined organic phases were dried (Na$_2$SO$_4$) and then evaporated in vacuo to afford the dipeptide as a white foam (2.84 g).

LC-MS (ESI): t$_R$=3.80 min (m/z=490.3 [M+H]$^+$).

General Procedure to Prepare N$^1$,N$^8$-dioleyl-N$^4$-(Aa)-spermidine (16)

The N-terminal-protected amino acid ((Aa)$_x$-(PG)$_y$: 1.1 eq.), HCTU (1.1 eq.), and diisopropylethylamine (3.2 eq.) were added to a solution of N$^1$,N$^8$-dioleyl-spermidine trifluoroacetate 6 in DMF (60 mM). The mixture was stirred at rt. under N$_2$ for 18 h when an equal volume of EtOAc was added. The organic mixture was washed successively with 5% aqueous KHSO$_4$ solution (3×), 5% aqueous K$_2$CO$_3$ solution (3×) and brine (1×), then dried (Na$_2$SO$_4$) and concentrated in vacuo. The residue was dissolved in EtOAc (10 mM) and an equal volume of 5.0N HCl in EtOAc was added. The reaction was stirred at rt. for 2 h and then concentrated in vacuo and the residue triturated with diethyl ether to afford an amorphous white solid which was purified by preparative MS-directed RP-HPLC (C-18, 5 μm; eluent A: Water+0.1% formic acid, eluent B: MeCN:Water [95:5]+0.1% formic acid; flow rate: 40 mL/min; detector (ESI-MS); method: 5-30% B in A over 15 min). The fraction containing the product was evaporated and the residue was dissolved in methanol and treated with 2.0N HCl in diethyl ether was added. After 10 min, the solvent was removed in vacuo and the residue was lyophilized to afford the surfactant hydrochloride 16 as a white solid.

Example 1

Aa=L-Dap

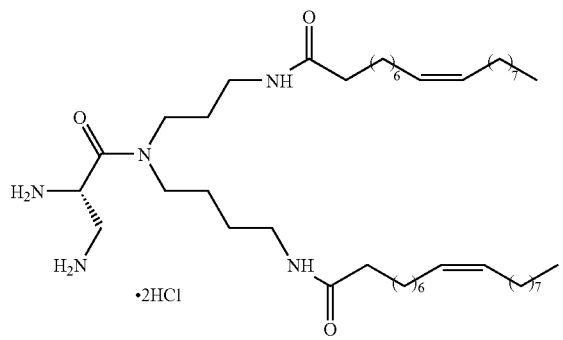

LC-MS (ESI): t$_R$=7.50 min (m/z=674.6 [M-Dap]$^+$ (100%), 760.7 [M+H]$^+$ (20%)); HRMS (ESI) m/z calcd (C$_{46}$H$_{90}$N$_5$O$_3$) 760.7044, found 760.7028 [M+H]$^+$.

Example 2

Aa=L-Dab

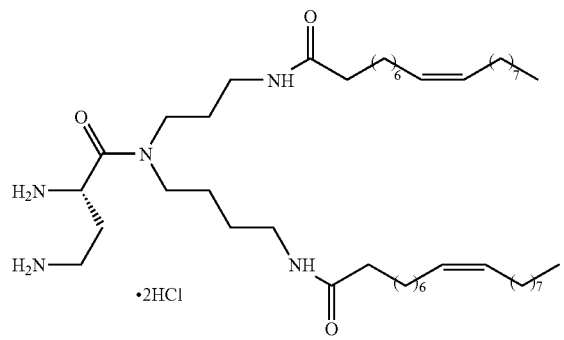

LC-MS (ESI): t$_R$=6.70 min (m/z=774.7 [M+H]$^+$ (50%)); HRMS (ESI) m/z calcd (C$_{47}$H$_{92}$N$_5$O$_3$) 774.7200, found 774.7197 [M+H]$^+$.

Example 3

Aa=L-Orn

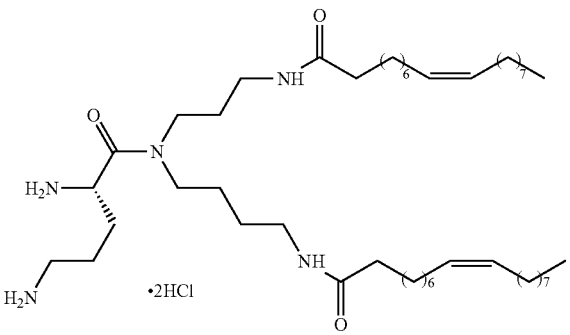

LC-MS (ESI): t$_R$=6.64 nm (m/z=788.7 [M+H]$^+$ (100%)); HRMS (ESI) m/z calcd (C$_{49}$H$_{94}$N$_5$O$_3$) 788.7357, found 788.7350 [M+H]$^+$.

Example 4

Aa=L-Lys

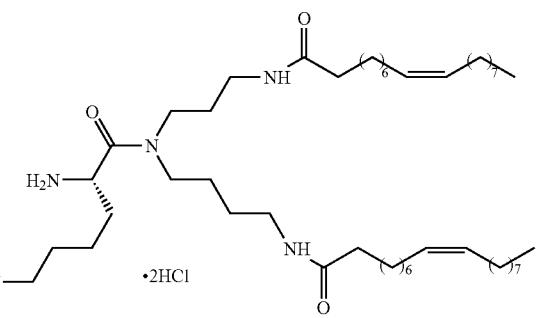

Example 5

Aa=D-Lys

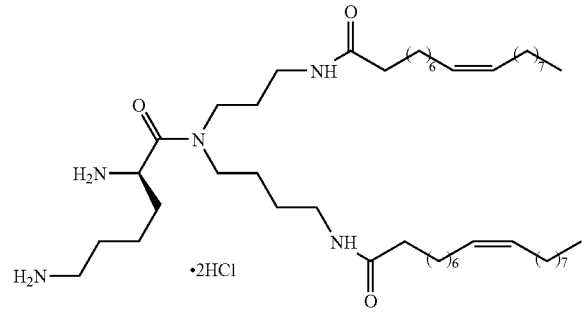

LC-MS (ESI): $t_R$=6.78 min (m/z=802.8 [M+H]$^+$ (100%)); HRMS (ESI) m/z calcd ($C_{49}H_{96}N_5O_3$) 802.7513, found 802.7524 [M+H]$^+$.

Example 6

Aa=L-Ser

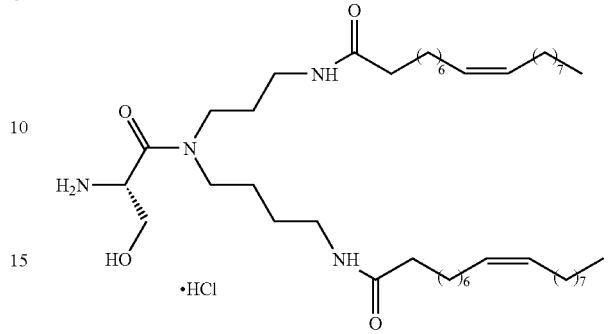

LC-MS (ESI): $t_R$=18.41 min (m/z=761.7 [M+H]$^+$ (100%)); HRMS (ESI) m/z calcd ($C_{46}H_{89}N_4O_4$) 761.6884, found 761.6888 [M+H]$^+$.

Example 7

Aa=L-Ser-L-Lys

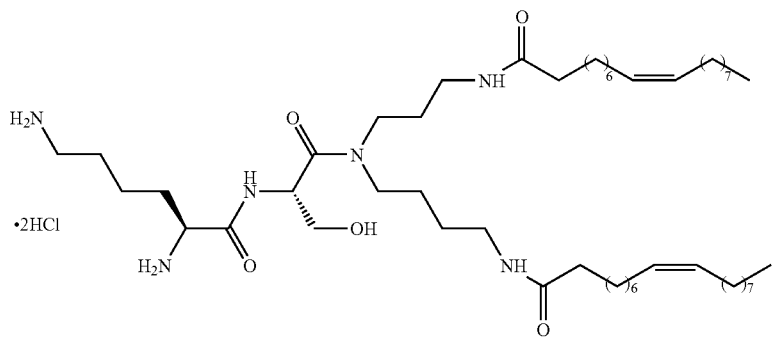

LC-MS (ESI): $t_R$=14.89 min (m/z=889.8 [M+H]$^+$ (100%)); HRMS (ESI) m/z calcd ($C_{52}H_{101}N_6O_5$) 889.7833, found 889.7829 [M+H]$^+$.

Example 8

Aa=L-Ser-D-Lys

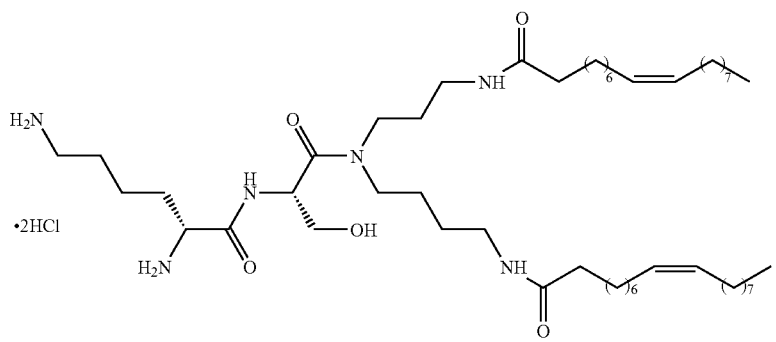

LC-MS (ESI): $t_R$=14.94 min (m/z=889.8 [M+H]$^+$ (100%)); HRMS (ESI) m/z calcd ($C_{52}H_{101}N_6O_5$) 889.7833, found 889.7842 [M+H]$^+$.

Example 9

Aa=(14)

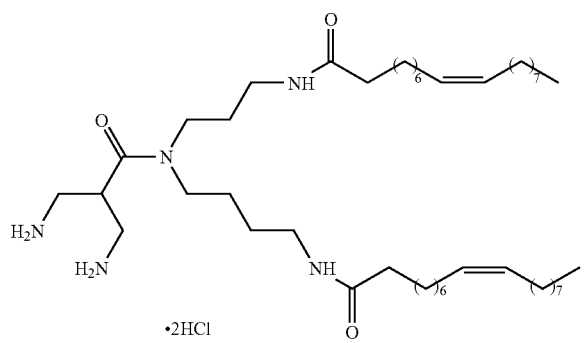

LC-MS (ESI): $t_R$=6.33 min (m/z=774.7 [M+H]$^+$ (100%)).

Example 10

Aa=(9)

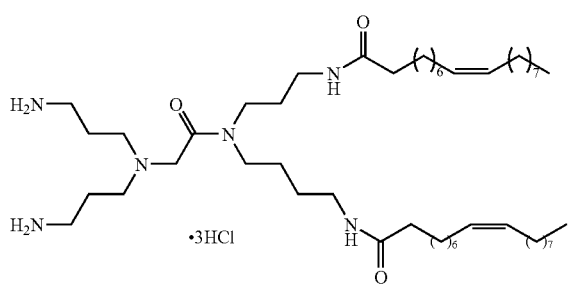

A solution of the bis-Boc carboxylic acid 9 (660 mg, 1.68 mmol) in CH$_2$Cl$_2$ (15 mL) containing TBTU (530 mg, 1.68 mmol) and diisopropylethylamine (1.5 mL 8.40 mmol) was added to N$^1$,N$^8$-dioleyl-spermidine bis(trifluoroacetate) 6 (1.00 g, 1.40 mmol). The mixture was stirred at rt. For 18 h, then concentrated in vacuo and the residue taken up in CH$_2$Cl$_2$ (100 mL) and washed successively with 5% aqueous KHSO$_4$ solution (25 mL), 5% aqueous K$_2$CO$_3$ solution (2×25 mL) and brine (50 mL). The organic phase was dried (Na$_2$SO$_4$) and evaporated in vacuo to leave an oil which was purified by column chromatography (silica gel) eluting with a mixture of CHCl$_3$-MeOH [90:10] to afford the intermediate bis-Boc carbamate as a colourless gum. The gum was dissolved in CH$_2$Cl$_2$ (25 mL) and treated with 5N HCl in EtOAc (10 mL). The resulting mixture was stirred at rt. for 2 h when the precipitated solid was collected by filtration, washed with anhydrous diethyl ether and dried in vacuo to afford Example 10 as a white powder.

LC-MS (ESI): $t_R$=12.65 min (m/z=845.8 [M+H]$^+$ (100%)); HRMS (ESI) m/z calcd (C$_{51}$H$_{101}$N$_6$O$_3$) 845.7935, found 845.7938 [M+H]$^+$.

General Procedure to Prepare N$^1$,N$^8$-dioleyl-N$^4$-[(14)-Aa]-spermidine (20)

The N-terminal-protected amino acid (2.6 eq.), HCTU (2.6 eq.), and DIEA (7.5 eq.) were added to a solution of Example 9 in DMF (80 mM). The mixture was stirred at rt. under N$_2$ for 18 h and then an equal volume of EtOAc was added. The organic mixture was washed successively with 5% aqueous KHSO$_4$ solution (3×), 5% aqueous K$_2$CO$_3$ solution (3×) and brine (1×), then dried (Na$_2$SO$_4$) and concentrated in vacuo. The residue was dissolved in EtOAc (10 mM) and an equal volume of 5.0N HCl in EtOAc was added. The reaction was stirred at rt. for 2 h and then concentrated in vacuo and the residue triturated with diethyl ether to afford an amorphous white solid which was purified by preparative MS-directed RP-HPLC(C-18, 5 μm; eluent A: Water+0.1% formic acid, eluent B: MeCN:Water [95:5]+0.1% formic acid; flow rate: 40 mL/min; detector (ESI-MS); method: 30-50% B in A over 15 min). The fraction containing the product was evaporated and the residue was dissolved in methanol and treated with 2.0M HCl in diethyl ether. After 10 nm, the solvent was removed in vacuo and the residue was lyophilized to afford the hydrochloride salt 20 as a white solid.

Example 11

Aa=L-Dab

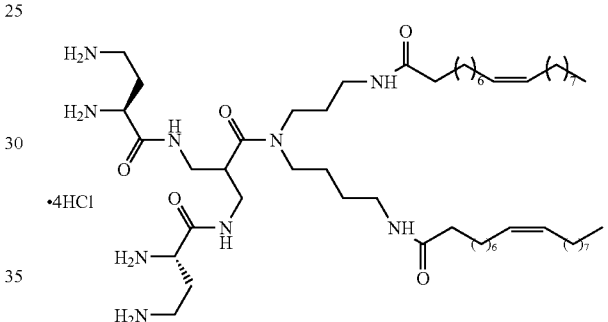

LC-MS (ESI): $t_R$=12.65 min (m/z=974.8 [M+H]$^+$ (100%)); HRMS (ESI) m/z calcd (C$_{55}$H$_{108}$N$_9$O$_5$) 974.8473, found 974.8473 [M+H]$^+$.

Example 12

Aa=L-Lys

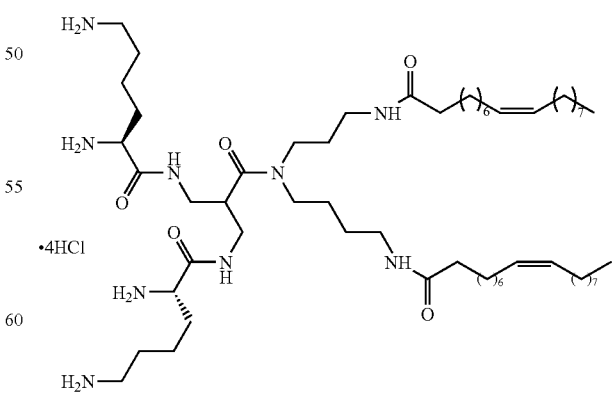

LC-MS (ESI): $t_R$=12.47 min (m/z=1030.9 [M+H]$^+$ (100%)); HRMS (ESI) m/z calcd (C$_{59}$H$_{116}$N$_9$O$_5$) 1030.9099, found 1030.9108 [M+H]$^+$.

Example 13

Aa=L-Ser-L-Lys

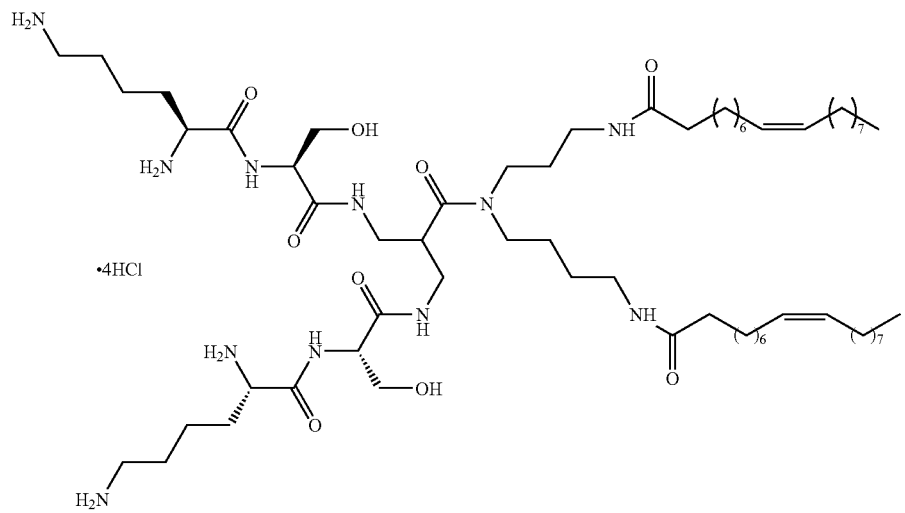

LC-MS (ESI): $t_R$=12.46 min (m/z=603.0 [M+2H]$^{2+}$ (100%), 1205.0 [M+H]$^+$ (85%)); HRMS (ESI) m/z calcd ($C_{65}H_{126}N_{11}O_9$) 1204.9740, found 1204.9755 [M+H]$^+$.

General Procedure to Prepare $N^1,N^8$-dioleyl-$N^4$-[(9)-Aa]-spermidine (20)

The amine hydrochloride Example 10 (Aa=9) (1.0 eq.) was added at rt. to a stirring solution of the N-terminal-protected amino acid ((Aa)$_x$(PG)$_y$; 2.2 eq.), 1-(3-dimethylaminopropyl)-3-ethylcarbodiimide hydrochloride (2.2 eq.) and diisopropylethylamine (6.0 eq.) in CH$_2$Cl$_2$ (approx. 20 mM). After 18 h, the reaction mixture was concentrated in vacuo, and the residue was dissolved in CH$_2$Cl$_2$ and washed successively with water, 5% aqueous K$_2$CO$_3$ solution, and brine. The organic phase was dried (Na$_2$SO$_4$) and concentrated in vacuo to leave an oil which was purified by column chromatography (silica gel) eluting with a mixture of MeOH:CHCl$_3$ [97:3] containing 0.2% triethylamine to afford the intermediate carbamate 19 as a colourless gum. The gum was dissolved in 5N HCl in EtOAc (5 mM) and the resulting solution stirred at rt. for 2 h. The precipitated solid was collected by filtration, washed with anhydrous diethyl ether and dried in vacuo to afford the hydrochloride salt 20 as a white powder.

Example 14

Aa=L-Dap

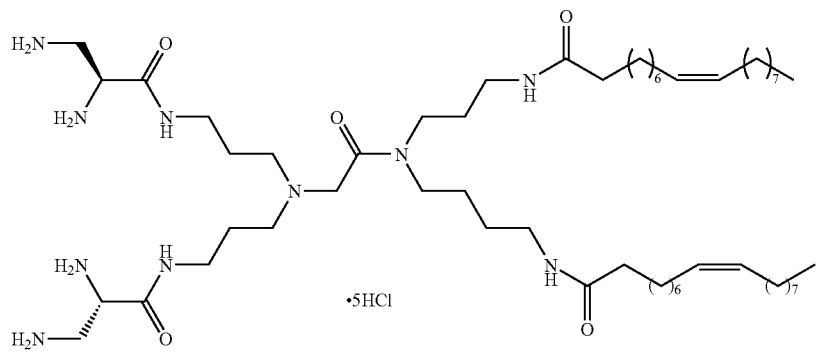

LC-MS (ESI): $t_R$=12.65 min (m/z=1017.9 [M+H]$^+$ (100%)); HRMS (ESI) m/z calcd ($C_{57}H_{113}N_{10}O_5$) 1017.8895, found 1017.8915 [M+H]$^+$.

Example 15
Aa=L-Dab
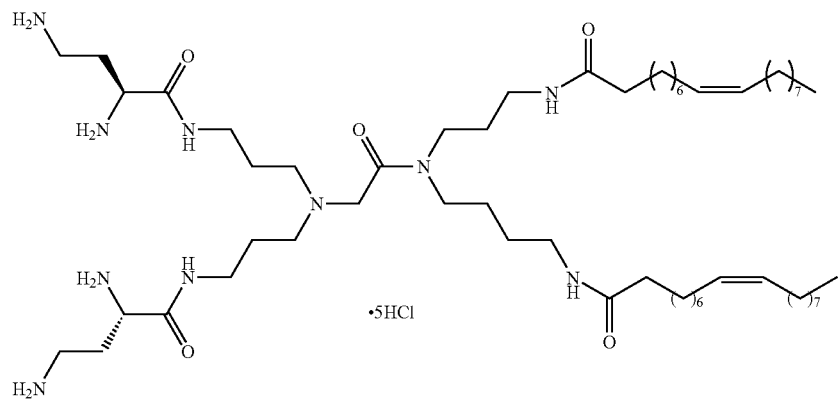
LC-MS (ESI): $t_R$=12.04 min (m/z=1045.9 [M+H]$^+$ (100%)); HRMS (ESI) m/z calcd ($C_{59}H_{117}N_{10}O_5$) 1045.9208, found 1045.9229 [M+H]$^+$.
Example 16
Aa=L-Lys
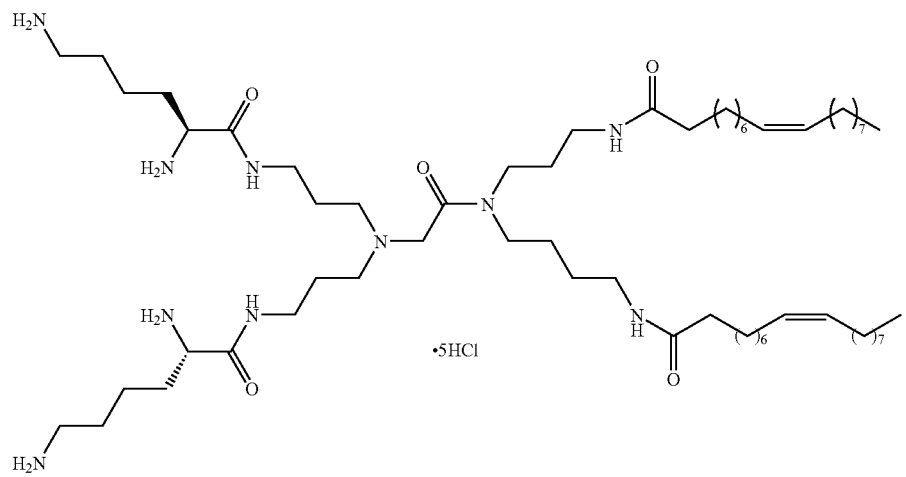
LC-MS (ESI): $t_R$=11.81 min (m/z=1101.9 [M+H]$^+$ (80%)); HRMS (ESI) m/z calcd ($C_{63}H125N_{10}O_5$) 1101.9834, found 1101.9818 [M+H]$^+$.

Example 17
Aa=D-Lys
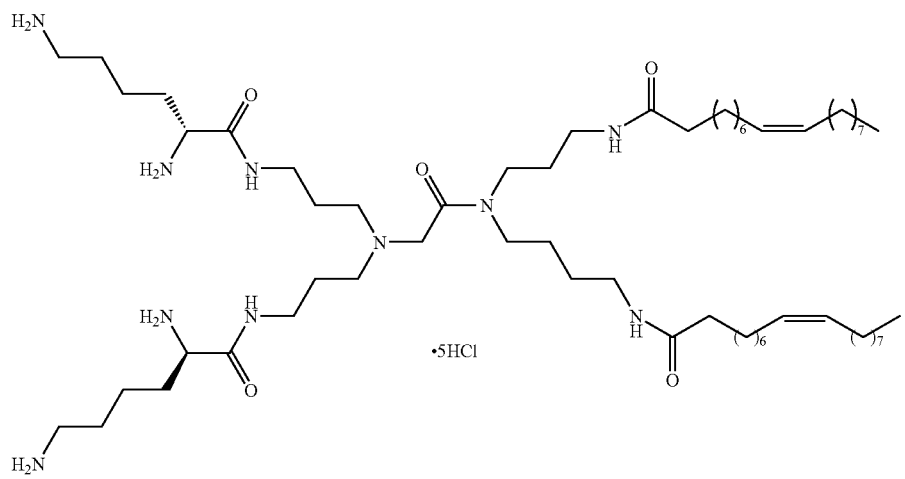
LC-MS (ESI): $t_R$=11.94 min (m/z=1101.9 [M+H]$^+$ (80%)); HRMS (ESI) m/z calcd ($C_{63}H_{125}N_{10}O_5$) 1101.9834, found 1101.9835 [M+H]$^+$.
Example 18
Aa=L-Ser
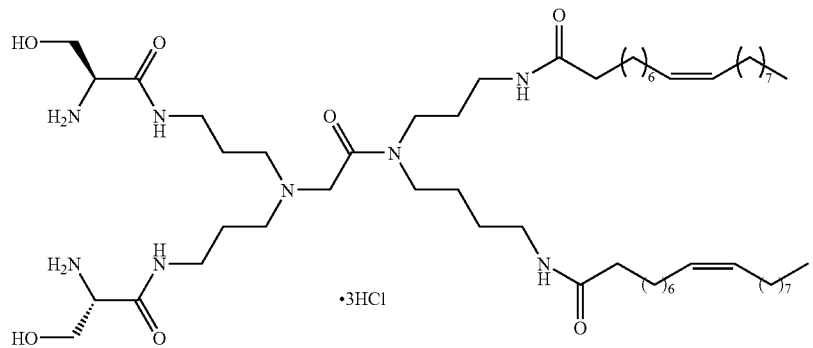
LC-MS (ESI): $t_R$=13.25 min (m/z=1019.8 [M+H]$^+$ (100%)); HRMS (ESI) m/z calcd ($C_{57}H_{111}N_8O_7$) 1019.8576, found 1019.8560 [M+H]$^+$.

Example 19

Aa=L-Ser-L-Lys

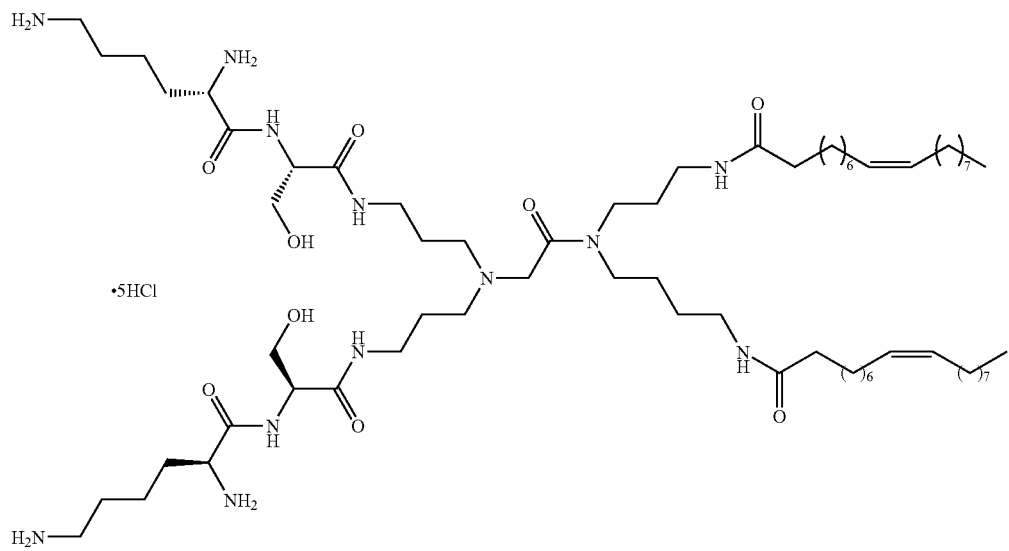

LC-MS (ESI): $t_R$=11.91 min (m/z=1276.0 [M+H]$^+$ (100%), HRMS (ESI) m/z calcd ($C_{69}H_{135}N_{12}O_9$) 1276.0475, found 1276.0447 [M+H]$^+$.

Example 20

Aa=(9)

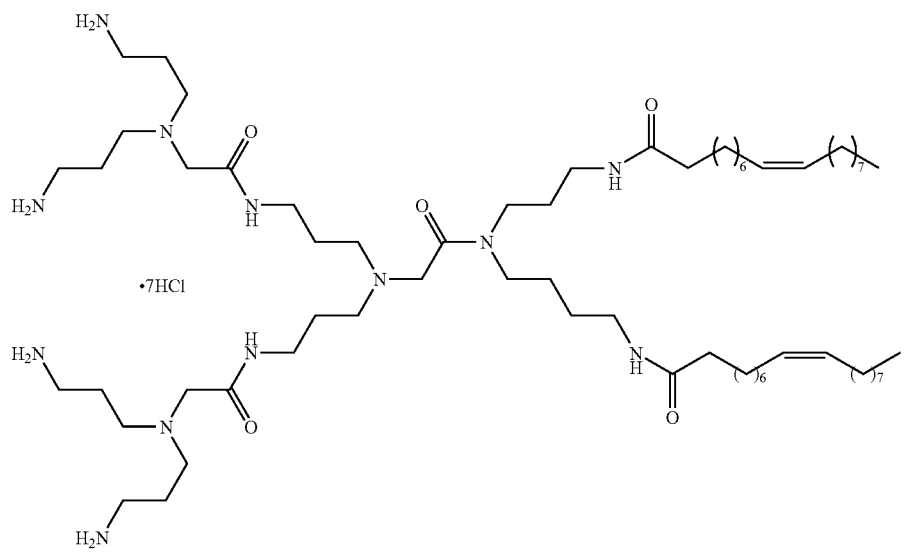

LC-MS (ESI): $t_R$=11.66 mm (m/z=1188.0 [M+H]$^+$ (100%)); HRMS (ESI) m/z calcd ($C_{67}H135N_{12}O_5$) 1188.0678, found 1188.0686 [M+H]$^+$.

Example 21

Transfection of Recombinant Plasmid Expressing GFP into Cells Using Spermidine-Based Surfactant Compounds Transfection studies were performed using the adherent cell lines CHO-K1, Caco-2 cells, HepG2 cells, and Ishikawa cells. Complete medium consisted of F12 (for CHO-K1), EMEM (for Caco-2) and DMEM (for HepG2, Ishikawa) supplemented with 10% v/v foetal bovine serum and 1×L-Glutamine. All media and supplements were obtained from Life Technologies.

In Vitro Gene Transfection

Cells were seeded into tissue culture treated 96-well plates (Costar) 16-18 hours prior to transfection at an approximate density of 2×10$^4$ cells/well. A 0.025 µg/µl plasmid solution was prepared in Optimem. The plasmid used was pCMV-eGFP obtained from Clontech. The spermidine surfactant compound was dissolved in Optimem as a 10× concentrate so as to achieve a final concentration of 20, 10, 5 and 2.5 µg/ml in the final reaction mixture. 10 μl of the spermidine surfactant compound was mixed with 10 ul of the plasmid for each well. The complex was incubated at room temperature for 10 minutes. The medium was removed from the cells in the plate and they were washed once with 100 μl PBS. The complex (20 μl) was added to each well and then 80 μl Optimem (serum-free) or growth medium (serum) was added to make a final volume of 100 μl. In the serum-free protocol, the plate was then incubated for 6 hours at 37° C. and the medium was then removed and fresh complete medium was added to each well and incubation continued for a further 18 hours. In the serum protocol, the plate was incubated for 24 h at 37° C.

Reporter gene assays were performed according to the manufacturer's guidelines (Roche Diagnostics). The medium was removed from the plate and the cells were washed once with 100 μl PBS. 100 μl reporter lysis buffer (50 mM HEPES pH 7.5, 2 mM EDTA, 0.05% triton×100, 2 mM DTT) was then added to each well. The plate was then placed at −80° C. for 15 min and subsequently allowed to thaw at room temperature. Fluorescence was then measured using a standard plate reader (Tecan Ultra, Tecan) with excitation wavelength 485 nm and emission wavelength 520 nm.

FIG. 7 shows the expression of GFP in Caco-2 cells that have been transfected with the aid of the compound of Examples 5, 3, 8, 7 and 10.

FIG. 8 shows the expression of GFP in HepG2 cells that have been transfected with the aid of the compound of Examples 5, 3, 8, 7 and 18.

FIG. 9 shows the expression of GFP in Ishikawa cells that have been transfected with the aid of the compound of Examples 5, 3, 8, 7, 14, 18 and 10.

FIG. 10 shows the expression of GFP in CHO-K1 cells that have been transfected with the aid of the compound of Examples 5, 3, 7 and 18.

Example 22

Transfection of siRNA into Cells Using Spermidine-Based Surfactant Compounds

Knockdown studies were performed using the adherent cell lines Ishikawa and MCF7. Complete medium consisted DMEM medium supplemented with 10% v/v foetal bovine serum and 1×L-Glutamine. All media and supplements were obtained from Life Technologies.

In Vitro siRNA Transfection

Cells were seeded into tissue culture treated 96-well plates (Costar) 16-18 hours prior to transfection at an approximate density of $2 \times 10^4$ cells/well. A 1 μM solution of siRNA (targeting JNK1 or non-targeting control) purchased from Dharmacon was prepared in Optimem. The Gemini lipid was dissolved in Optimem as a 10× concentrate so as to achieve a final concentration of 5 μg/ml in final the reaction mixture. The commercial reagent lipofectamine 2000 was used at a final concentration of 2.5 μg/ml, siLentFect at 1 μg/ml and X-tremeGene at 0.5 μl/well. A 10 μl sample of the Gemini (commercial) lipid was mixed with 10 μl of the siRNA for each well. The complex was incubated at room temperature for 10 minutes. The medium was removed from the cells in the plate and they were washed once with 100 μl PBS. The complex (20 μl) was added to each well and then 80 μl growth medium was added to make a final volume of 100 μl. and the plate was incubated for 24 h at 37° C. At this time point the cells were washed once using 100 μl PBS and then lysed in 100 μl RNA lysis buffer (Promega). Standard quantitative RT-PCR (Taqman) was carried out to determine the relative abundance of JNK1 compared to the housekeeping gene GAPDH in both JNK1 siRNA targeted and non-targeted cells. The degree of knockdown was expressed as a ratio of treated (JNK1) copies of Jnk1 to control (non-targeted) copies of JNK1.

FIG. 11 shows the knockdown of JNK1 in MCF-7 cells that have been transfected with the aid of the compound of Examples 10, 5 and 3.

FIG. 12 shows the knockdown of JNK1 in Ishikawa cells that have been transfected with the aid of the compound of Examples 10, 5 and 3.

All publications, including but not limited to patents and patent applications, cited in this specification are herein incorporated by reference as if each individual publication were specifically and individually indicated to be incorporated by reference herein as though fully set forth.

Figure 1:
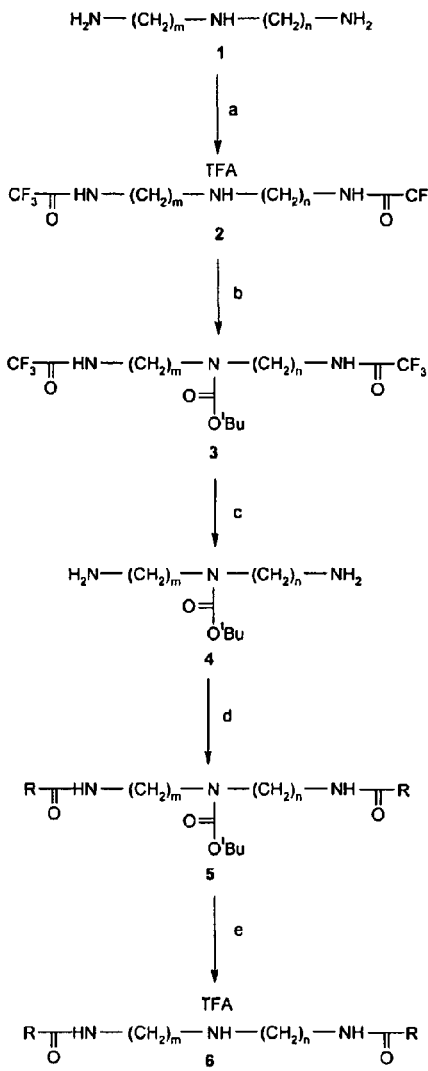
FIG. 1 shows a general scheme for the synthesis of a protected (Aa) group 6 useful in the synthesis of molecules of the invention.
Figure 2:
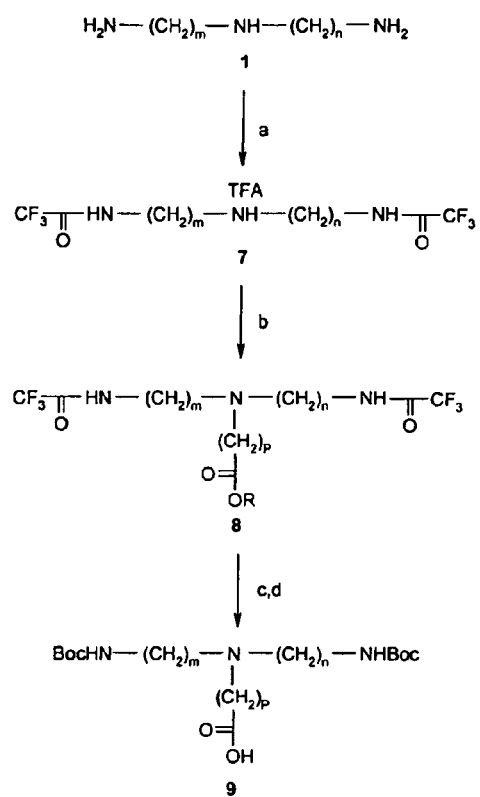
FIG. 2 shows a general scheme for the synthesis of a protected (Aa) group 9 useful in the synthesis of molecules of the invention.
Figure 3:
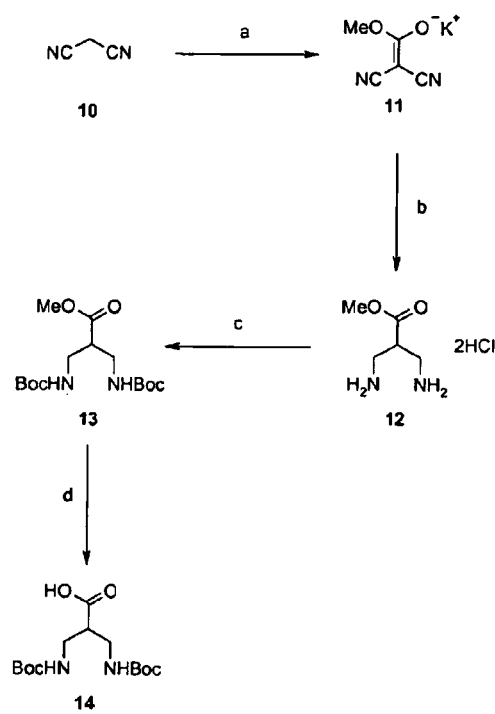
FIG. 3 shows a general scheme for the synthesis of an advanced intermediate 14 useful in the synthesis of molecules of the invention.
Figure 4:
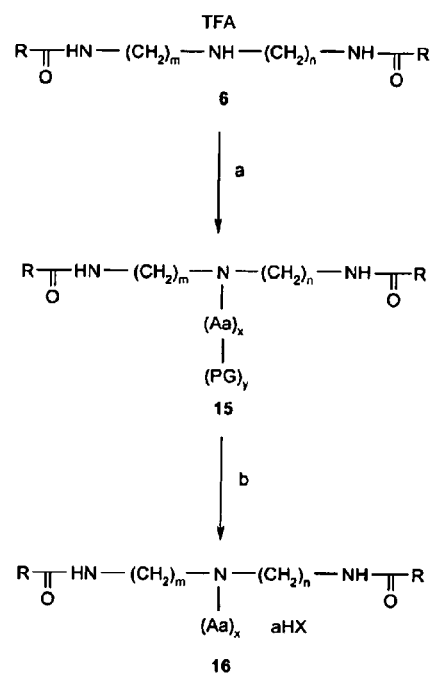
FIG. 4 shows a general scheme for the synthesis of molecules according to one general embodiment of the invention.
Figure 5:
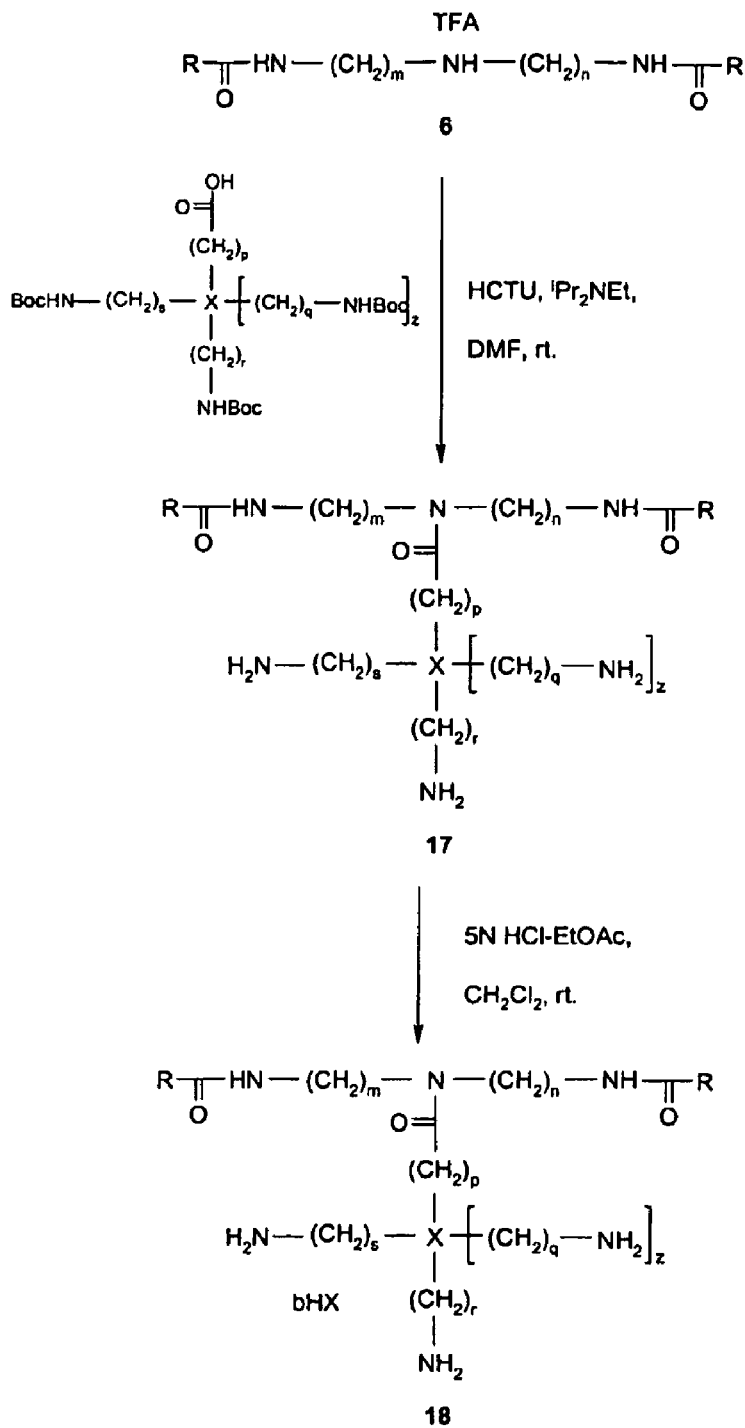
FIG. 5 shows a general scheme for the synthesis of molecules according to a further general embodiment of the invention.
Figure 6:
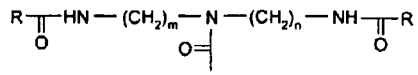
FIG. 6 shows a general scheme for the synthesis of molecules according to a further general embodiment of the invention.
Figure 6:
Figure 6:
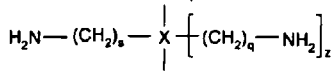
Figure 6:
Figure 6:
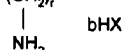
Figure 6:
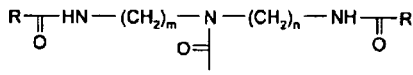
Figure 6:
Figure 6:
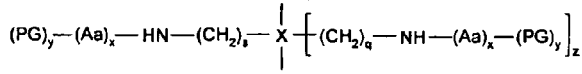
Figure 6:
Figure 6:
Figure 6:
Figure 6:
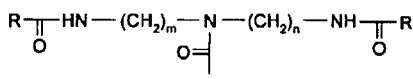
Figure 6:
Figure 6:
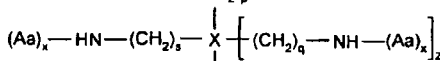
Figure 6:
Figure 6:
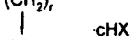
Figure 7:
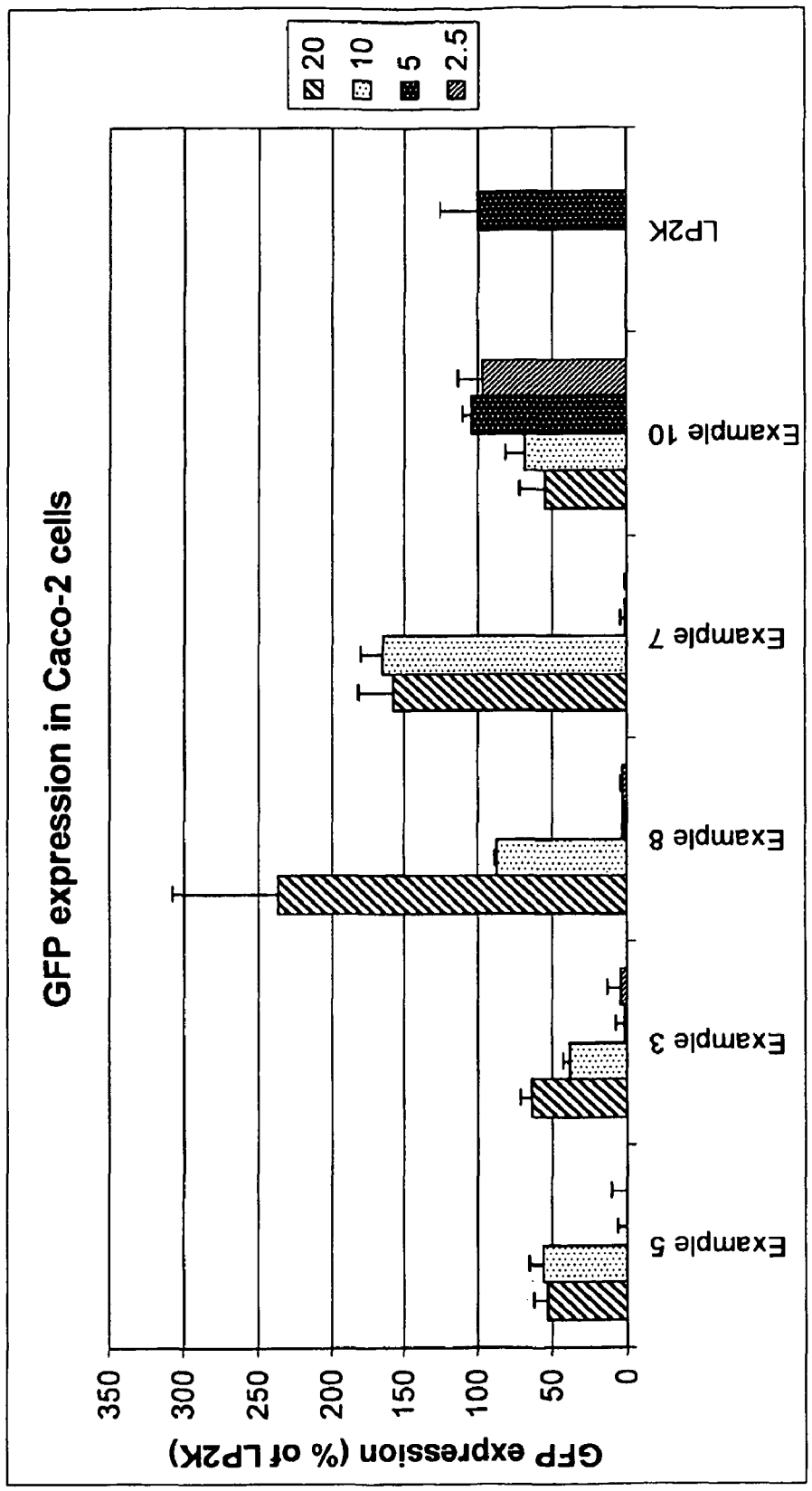
FIG. 7 shows the expression of GFP in Caco-2 cells that have been transfected with the aid of the compound of Examples 5, 3, 8, 7 and 10. The concentrations of the compounds of the examples is given in ug/ml. LP2K denotes lipofectamine 2000™.
Figure 8:
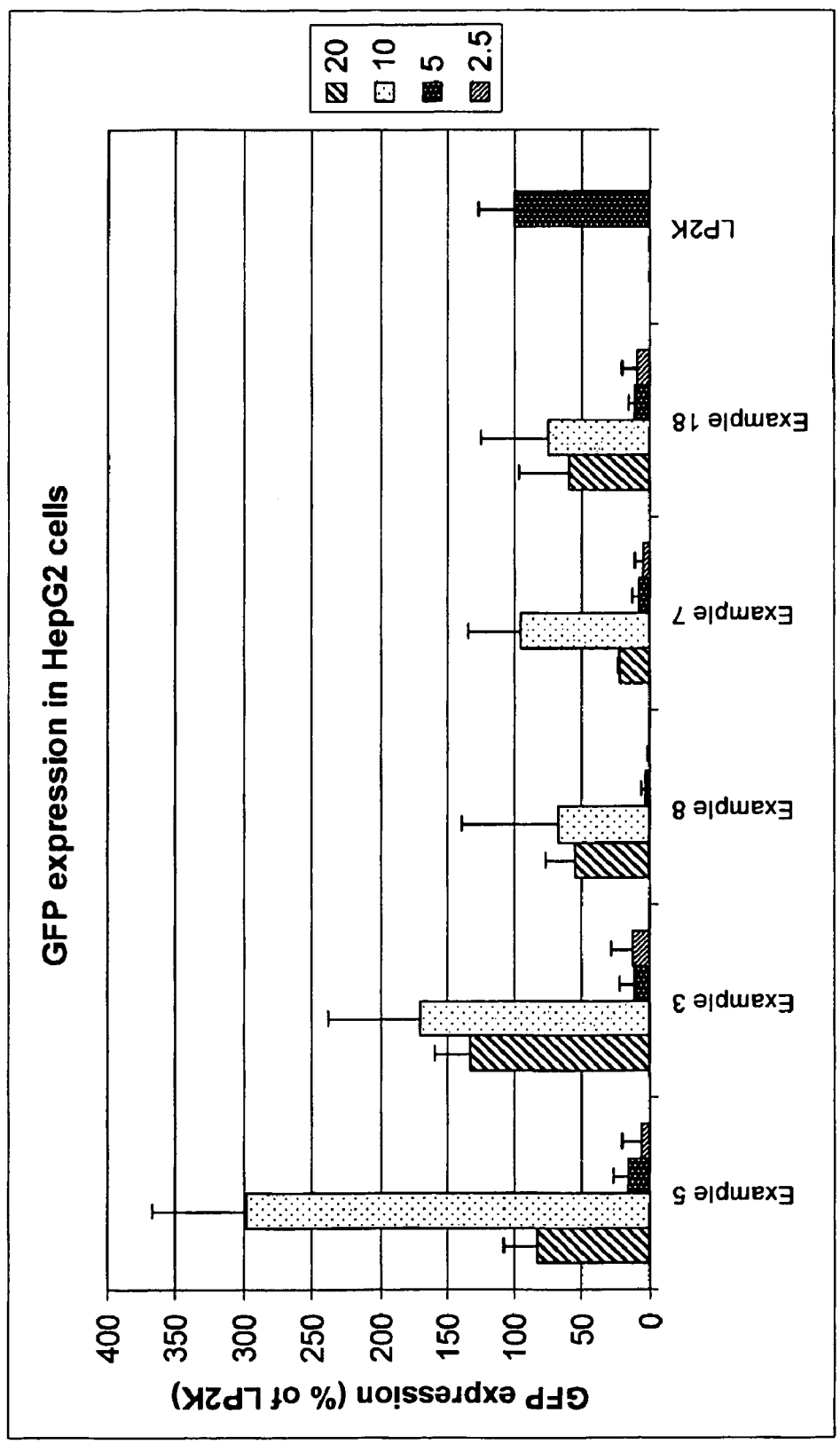
FIG. 8 shows the expression of GFP in HepG2 cells that have been transfected with the aid of the compound of Examples 5, 3, 8, 7 and 18. The concentrations of the compounds of the examples is given in ug/ml. LP2K denotes lipofectamine 2000™.
Figure 9:
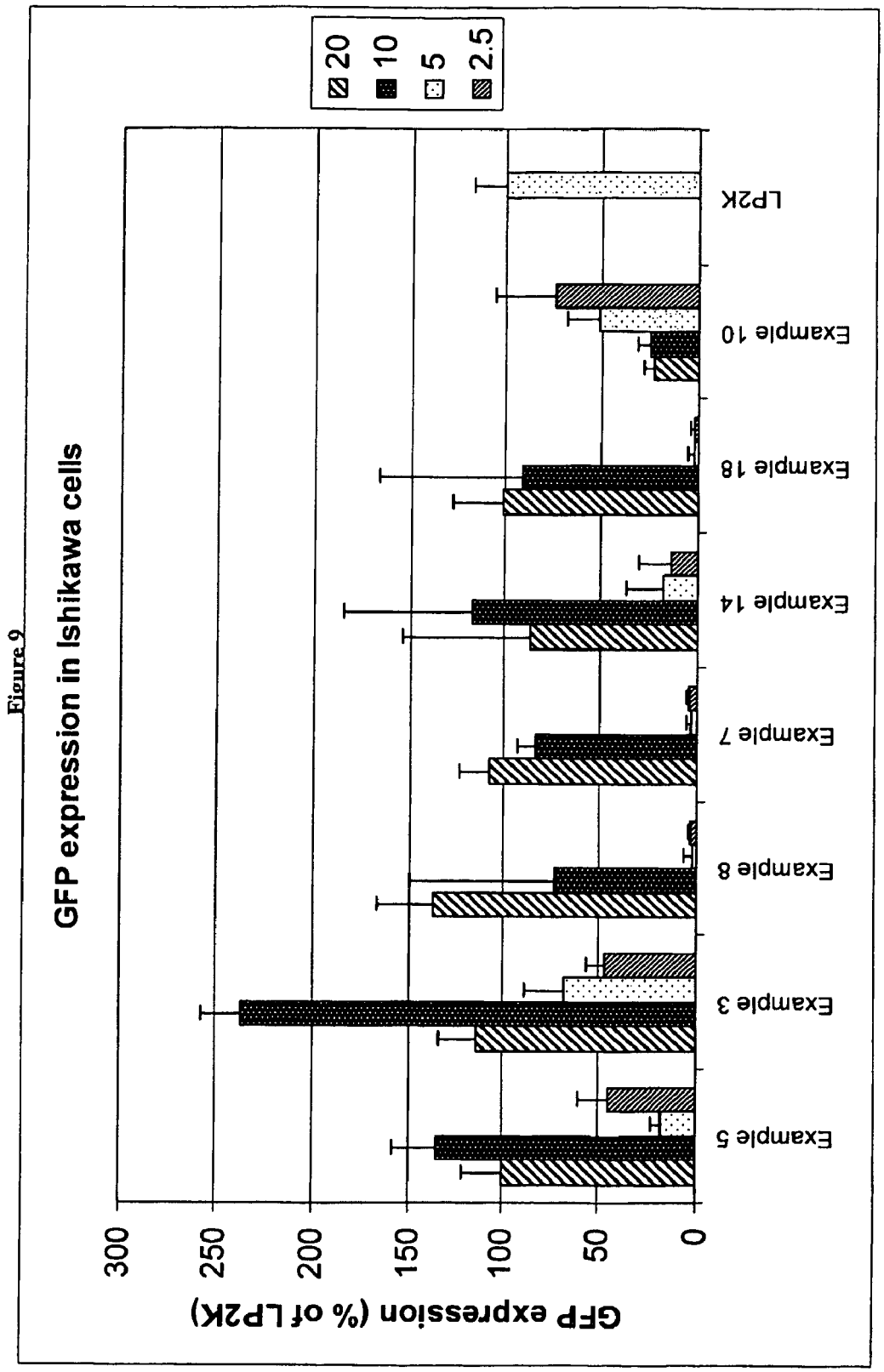
FIG. 9 shows the expression of GFP in Ishikawa cells that have been transfected with the aid of the compound of Examples 5, 3, 8, 7, 14, 18 and 10. The concentrations of the compounds of the examples is given in ug/ml. LP2K denotes lipofectamine 2000™.
Figure 10:
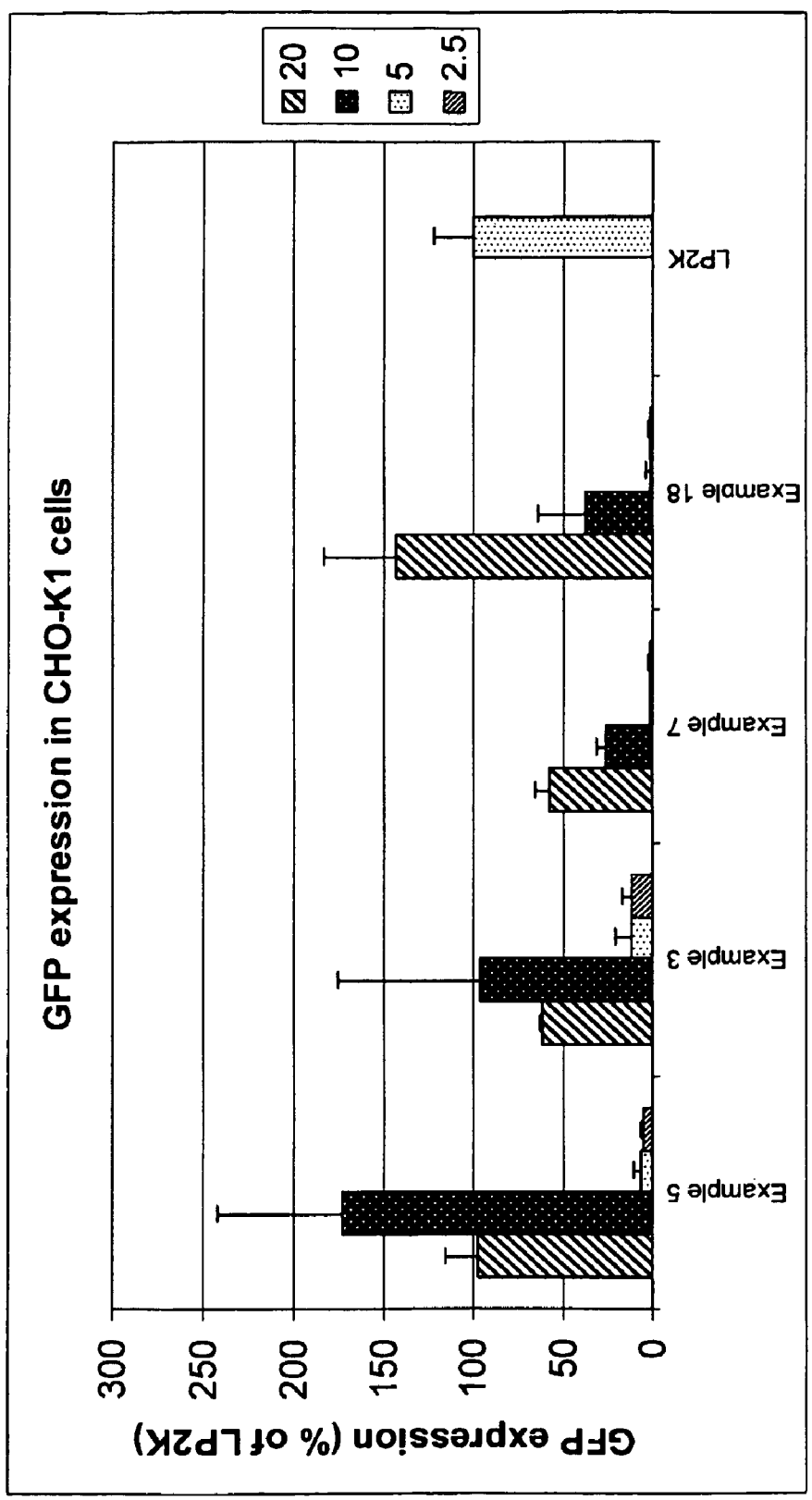
FIG. 10 shows the expression of GFP in CHO-K1 cells that have been transfected with the aid of the compound of Examples 5, 3, 7 and 18. The concentrations of the compounds of the examples is given in ug/ml. LP2K denotes lipofectamine 2000™.
Figure 11:
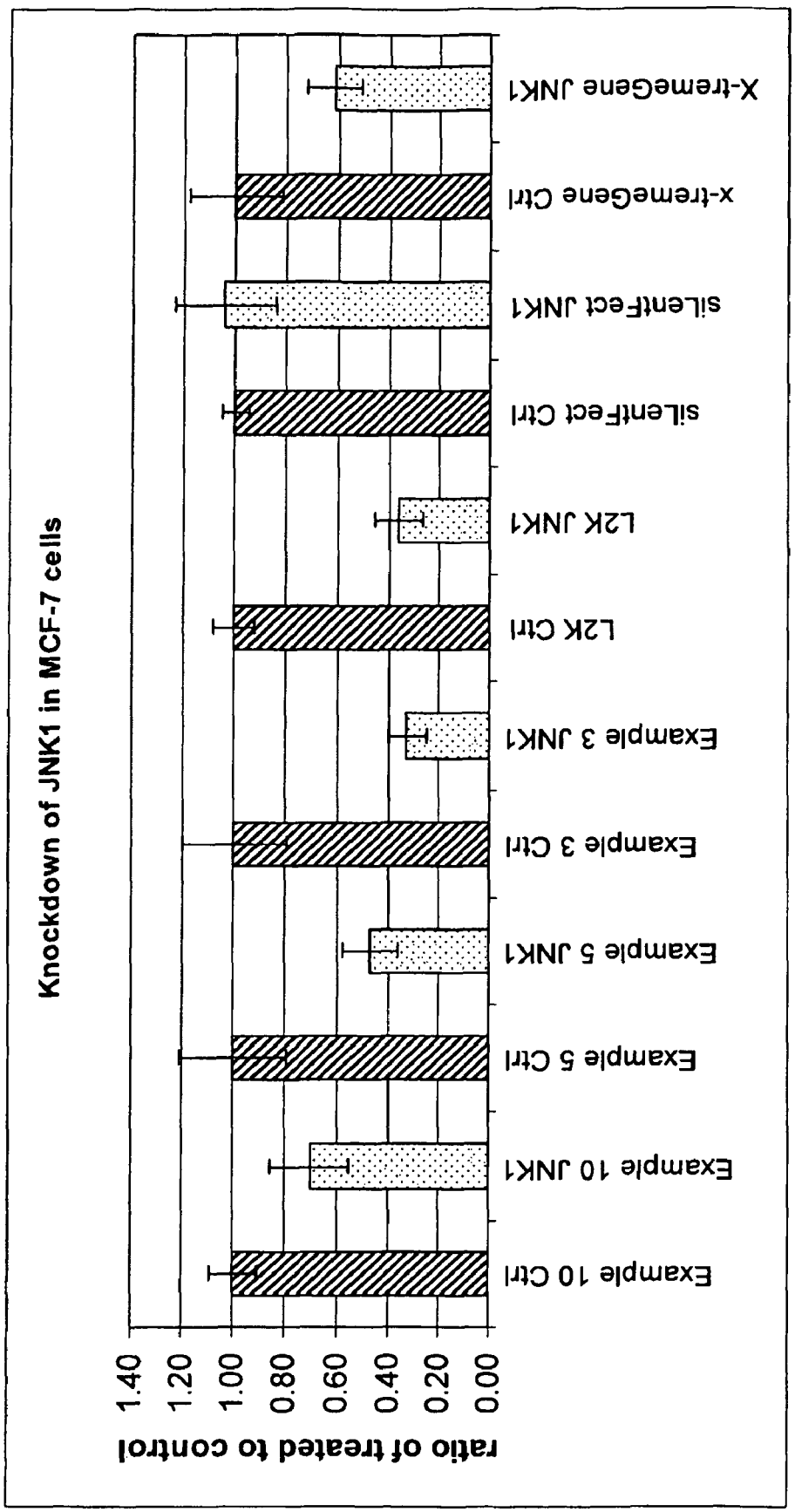
FIG. 11 shows the knockdown of JNK1 in MCF-7 cells that have been transfected with the aid of the compound of Examples 10, 5 and 3. L2K denotes lipofectamine 2000™.
Figure 12:
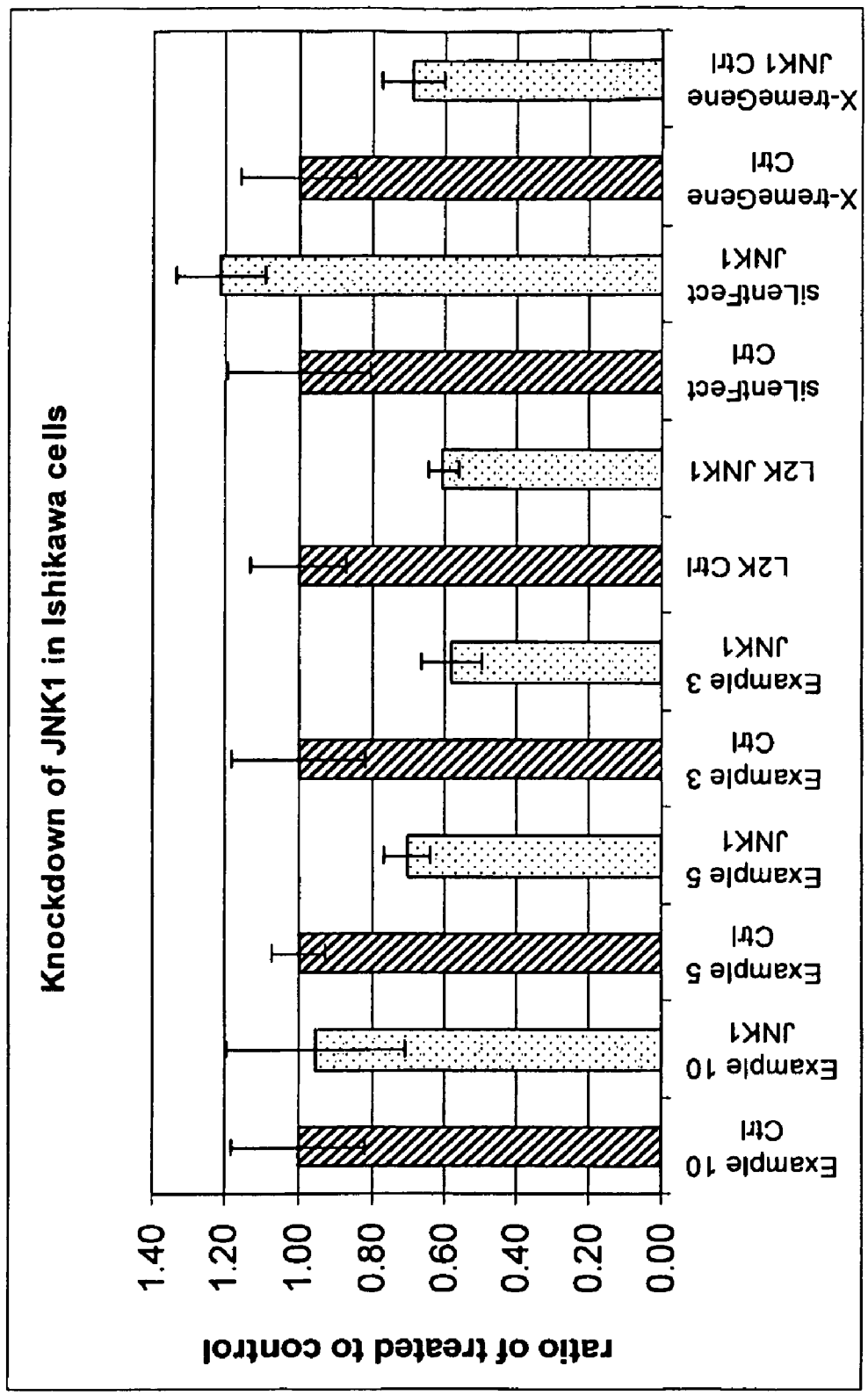
FIG. 12 shows the knockdown of JNK1 in Ishikawa cells that have been transfected with the aid of the compound of Examples 10, 5 and 3. L2K denotes lipofectamine 2000™.

The invention claimed is:

1. A compound having the general structure of formula (I):

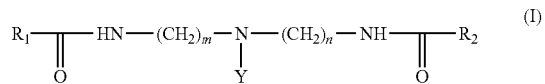

where Y is either:
(Aa)$_x$ or a group of formula (II)

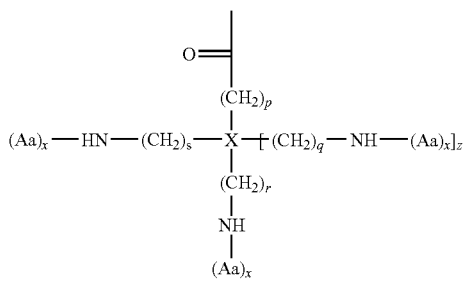

wherein
R$_1$ and R$_2$, which may be the same or different, is a saturated or unsaturated, linear or branched hydrocarbon chain of up to 24 carbon atoms
m is 1 to 10;
n is 1 to 10;
Aa, which may be the same or different at each occurrence, is (H$_2$N(CH$_2$)$_3$)$_2$N(CH$_2$)C(O))—, (H$_2$NCH$_2$)$_2$CHC(O)—, or an enantiomer of HOCH$_2$CH(NH$_2$)C(O)—, NH$_2$(CH$_2$)$_4$CH(NH$_2$)C(O)—, NH$_2$(CH$_2$)$_3$CH(NH$_2$)C(O)—, NH$_2$CH$_2$CH$_2$CH(NH$_2$)C(O)—, NH$_2$CH$_2$CH(NH$_2$)C(O)—, or H$_2$N(CH$_2$)$_4$CH(NH$_2$)C(O)NHCH(CH$_2$OH)C(O)—;
x is 1;
p is 0 to 6;
q is 1 to 6;
r is 1 to 6;
s is 1 to 6;
z is 0 or 1;
X is N, CH or C with the proviso that when X is N, z is 0 or 1; when X is CH, z is 0; and when X is C, z is 1;
or a pharmaceutically acceptable salt thereof.

2. A compound according to claim 1 in which m is 3 to 6.
3. A compound according to claim 2 in which n is 3 to 6.
4. A compound according to claim 1 in which Y is (Aa)$_x$.
5. A compound according to claim 1 in which Y is a group of formula (II)

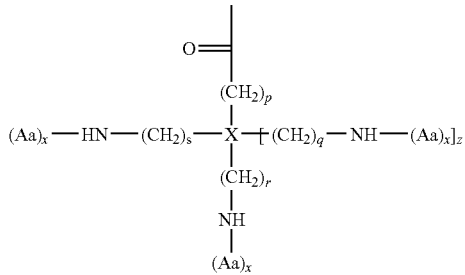

where
x 1;
p is 0 to 6;
q is 1 to 6;
r is 1 to 6;
s is 1 to 6;
z is 0 or 1;
X is N, CH or C with the proviso that when X is N, z is 0 or 1; when X is CH, z is 0; and when X is C, z is 1.

6. A compound according to claim 5 in which p is 1.
7. A compound according to claim 6 in which r is 1 or 3.
8. A compound according to claim 7 in which s is 1 or 3.
9. A compound according to claim 8 in which q is 1 or 3.
10. A compound according to claim 1 in which the R$_1$ or R$_2$ saturated or unsaturated, linear or branched hydrocarbon chain of up to 24 carbon atoms has 12 or more carbon atoms.
11. A compound according to claim 1 in which the R$_1$ or R$_2$ saturated or unsaturated, linear or branched hydrocarbon chain of up to 24 carbon atoms is selected from the group consisting of:

—(CH$_2$)$_{10}$CH$_3$
—(CH$_2$)$_{12}$CH$_3$
—(CH$_2$)$_{14}$CH$_3$
—(CH$_2$)$_{16}$CH$_3$
—(CH$_2$)$_{18}$CH$_3$
—(CH$_2$)$_{20}$CH$_3$
—(CH$_2$)$_7$CH═CH(CH$_2$)$_5$CH$_3$ natural mixture
—(CH$_2$)$_7$CH═CH(CH$_2$)$_7$CH$_3$ natural mixture
—(CH$_2$)$_7$CH═CH(CH$_2$)$_5$CH$_3$ Cis
—(CH$_2$)$_7$CH═CH(CH$_2$)$_7$CH$_3$ Cis
—(CH$_2$)$_7$CH═CH(CH$_2$)$_5$CH$_3$ Trans
—(CH$_2$)$_7$CH═CH(CH$_2$)$_7$CH$_3$ Trans
—(CH$_2$)$_7$CH═CHCH$_2$CH═CH(CH$_2$)$_4$CH$_3$
—(CH$_2$)$_7$(CH═CHCH$_2$)$_3$CH$_3$
—(CH$_2$)$_3$CH═CH(CH$_2$CH═CH)$_3$(CH$_2$)$_4$CH$_3$
—(CH$_2$)$_7$CHCH(CH$_2$)$_7$CH$_3$
—CH$_2$CH(CH$_3$)[CH$_2$CH$_2$CH$_2$CH(CH$_3$)]$_3$CH$_3$
and —(CH$_2$)$_{22}$CH$_3$.

12. The compound of formula:

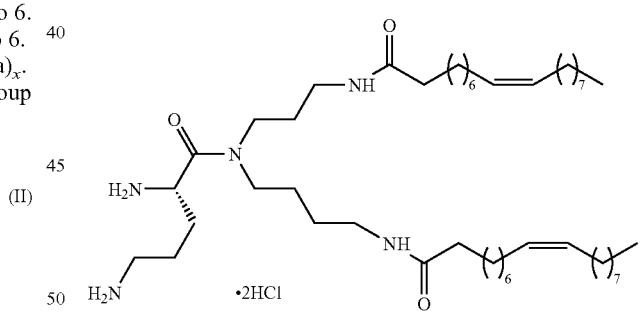

13. The compound of formula:

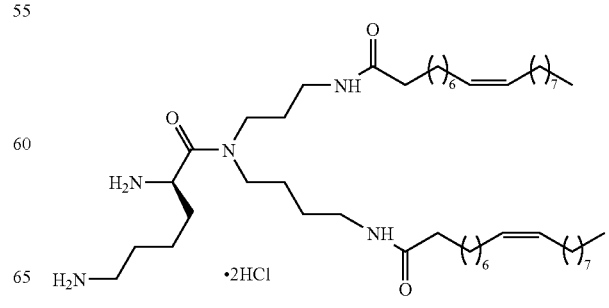

14. The compound of formula:
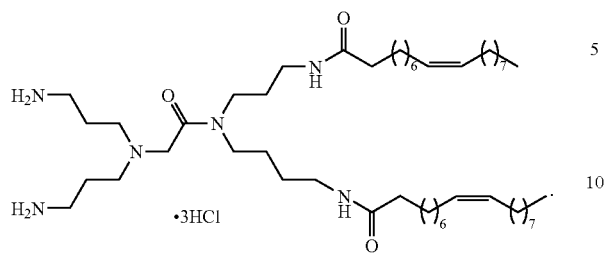
15. The compound of formula:
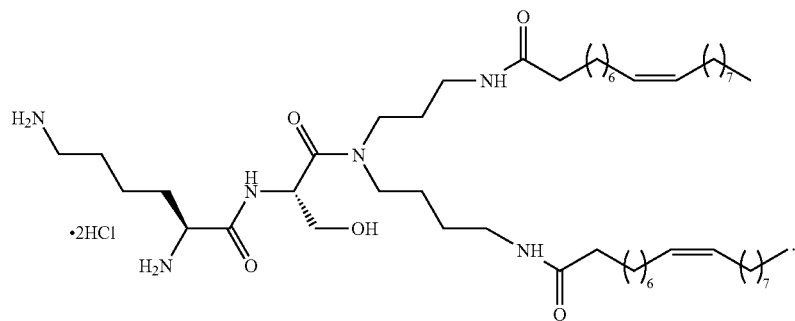
16. A method of transfecting polynucleotides into cells in vivo for gene therapy, which method comprises administering a compound of claim 1 together with, or separately from, the gene therapy vector.
* * * * *